United States Patent
Irisawa

(10) Patent No.: US 9,717,419 B2
(45) Date of Patent: Aug. 1, 2017

(54) OPTICAL FIBER CABLE, METHOD OF MANUFACTURING THE SAME, AND LIGHT SOURCE MODULE INCLUDING THE SAME

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/391,514

(22) Filed: Dec. 27, 2016

(65) Prior Publication Data

US 2017/0105626 A1 Apr. 20, 2017

Related U.S. Application Data

(63) Continuation of application No. PCT/JP2015/003188, filed on Jun. 25, 2015.

(30) Foreign Application Priority Data

Jun. 30, 2014 (JP) ................ 2014-133773

(51) Int. Cl.
*G02B 6/38* (2006.01)
*A61B 5/00* (2006.01)
(Continued)

(52) U.S. Cl.
CPC .......... *A61B 5/0095* (2013.01); *A61B 8/4444* (2013.01); *A61B 8/4483* (2013.01);
(Continued)

(58) Field of Classification Search
CPC ....... A61B 5/0095; A61B 8/4444; A61B 8/56; A61B 8/4483; A61B 8/461; G02B 6/3887; G01N 21/1702; G01N 2201/08
See application file for complete search history.

(56) References Cited

U.S. PATENT DOCUMENTS

| 2010/0174197 | A1 | 7/2010 | Nakajima et al. |
| 2014/0079354 | A1* | 3/2014 | Aoki ........................ G02B 6/38 385/72 |
| 2016/0270667 | A1 | 9/2016 | Nakajima et al. |

FOREIGN PATENT DOCUMENTS

| JP | 2-77705 A | 3/1990 |
| JP | 2000-171665 A | 6/2000 |

(Continued)

OTHER PUBLICATIONS

International Search Report for PCT/JP2015/003188 (PCT/ISA/210) mailed on Sep. 1, 2015.
(Continued)

*Primary Examiner* — John M Bedtelyon
(74) *Attorney, Agent, or Firm* — Birch, Stewart, Kolasch & Birch, LLP

(57) ABSTRACT

A plug that is engaged with a receptacle for light emission of a light source unit that emits a light beam having a flat-shaped cross section and an optical fiber having a burr defect in a part of an outer peripheral portion of an incidence end surface on which the light beam is incident are included. The plug is attached to an incidence end portion of the optical fiber in an arrangement in which the burr defect is located in a short axis direction of a cross section on the incidence end surface of the light beam incident on the incidence end surface in a state in which the plug is engaged with the receptacle.

18 Claims, 15 Drawing Sheets

(51) Int. Cl.
*A61B 8/00* (2006.01)
*G01N 21/17* (2006.01)

(52) U.S. Cl.
CPC ........... *A61B 8/461* (2013.01); *A61B 8/56* (2013.01); *G01N 21/1702* (2013.01); *G02B 6/3887* (2013.01); *G01N 2201/08* (2013.01)

(56) References Cited

FOREIGN PATENT DOCUMENTS

| JP | 2004-117916 A | 4/2004 |
| JP | 2009-31262 A | 2/2009 |
| JP | 2013-13713 A | 1/2013 |

OTHER PUBLICATIONS

Kobayashi et at., "Optical fiber connection realizing over 60-dB return loss with fiber physical contact", IEICE Electronics Society, Taikai Koen Ronbunshu 1, p. 188, 1995.
Written Opinion of the International Searching Authority for PCT/JP2015/003188 (PCT/ISA/237) mailed on Sep. 1, 2015.

\* cited by examiner

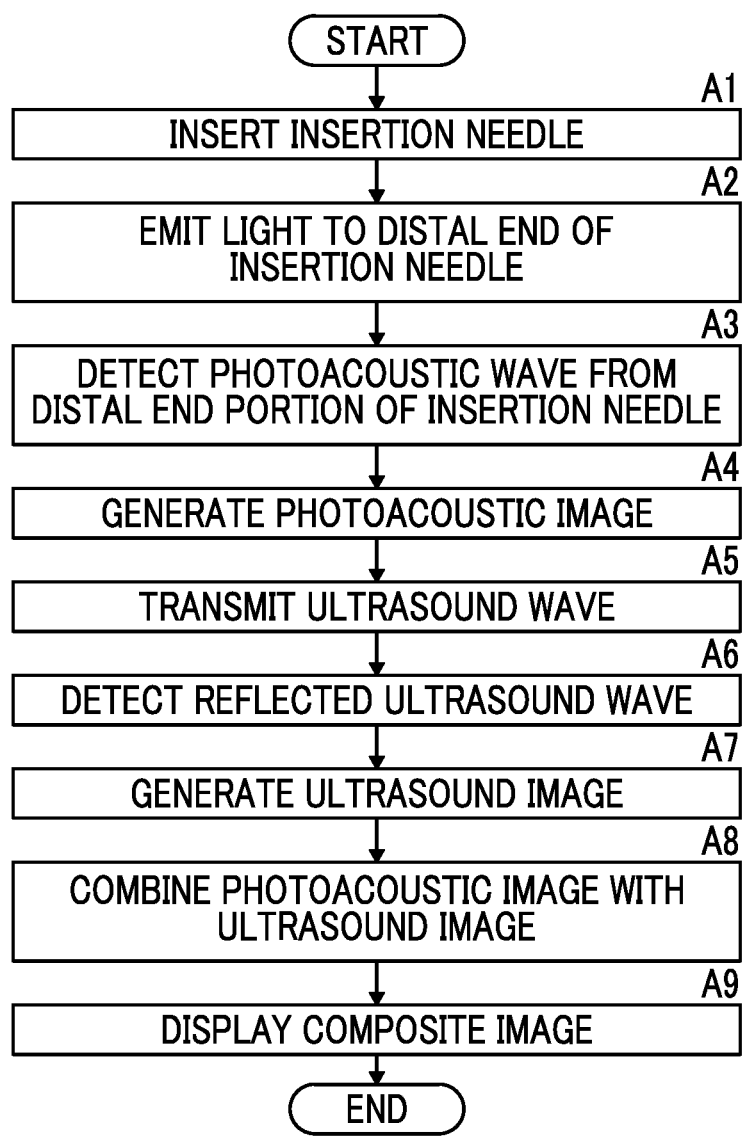

OPTICAL FIBER CABLE, METHOD OF MANUFACTURING THE SAME, AND LIGHT SOURCE MODULE INCLUDING THE SAME

CROSS-REFERENCE TO RELATED APPLICATIONS

This application is a Continuation of PCT International Application No. PCT/JP2015/003188 filed on Jun. 25, 2015, which claims priority under 35 U.S.C. §119(a) to Japanese Patent Application No. 2014-133773 filed on Jun. 30, 2014. Each of the above applications is hereby expressly incorporated by reference, in its entirety, into the present application.

BACKGROUND OF THE INVENTION

1. Field of the Invention

The present invention relates to an optical fiber cable with a plug that guides light, a method of manufacturing the same, and a light source module including the optical fiber cable.

2. Description of the Related Art

As a kind of image examination method capable of examining the state of the inside of a subject (for example, a body) in a non-invasive manner, ultrasonography is known. In ultrasound examination, an ultrasound probe capable of transmitting and receiving ultrasound waves is used. When ultrasound waves are transmitted to a subject from the ultrasound probe, the ultrasound waves propagate through the subject to be reflected on tissue interfaces. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of a subject using the photoacoustic effect is known. In general, in photoacoustic imaging, pulsed laser light, such as a laser pulse, is emitted into the subject. In the subject, tissue absorbs the energy of the pulsed laser light, and ultrasound waves (photoacoustic waves) due to adiabatic expansion due to the energy are generated. By detecting the photoacoustic waves using an ultrasound probe or the like and forming a photoacoustic image based on the detection signal, it is possible to visualize the inside of the subject based on the photoacoustic waves.

For example, JP2009-31262A discloses a combination of biological information imaging using photoacoustic waves and treatment using an insertion needle. In JP2009-31262A, an affected part such as a tumor, a part suspected to be an affected part, or the like is found by generating a photoacoustic image and observing the image. In order to examine such a part more precisely or in order to perform injection into the affected part, sampling of cells, injection into the affected part, and the like are performed using an insertion needle, such as an injection needle or a cytodiagnosis needle. In JP2009-31262A, it is possible to perform insertion while observing the affected part using a photoacoustic image.

In addition, JP2013-13713A discloses a method of guiding light to the vicinity of the distal end of an insertion needle, which has an optical fiber inserted thereinto, using the insertion needle, generating photoacoustic waves in the vicinity of the insertion needle, and generating a photoacoustic image based on the photoacoustic waves. According to this method, since it is possible to guide light to a deep portion of the subject unlike in the method disclosed in JP2009-31262A, it is possible to check the insertion needle present in the deep portion.

SUMMARY OF THE INVENTION

Usually, an insertion needle such as that disclosed in JP2013-13713A is discarded once it is used, and the optical fiber inserted into the inside of the insertion needle is also discarded along with the insertion needle.

On the other hand, in the manufacturing of an optical fiber cable, a step of polishing the end surface is generally performed in order to remove a burr formed on the end surface of the optical fiber. However, this polishing step is time-consuming work, and is one of the factors that increase the cost when manufacturing the optical fiber cable.

The present invention has been made in view of the aforementioned problem, and it is an object of the present invention to provide an optical fiber cable that can be manufactured at lower cost, a method of manufacturing the same, and a light source module comprising the same.

In order to solve the aforementioned problem, an optical fiber cable of the present invention comprises: a plug that is engaged with a receptacle for light emission of a light source unit that emits a light beam having a flat-shaped cross section; and an optical fiber having a burr defect in a part of an outer peripheral portion of an incidence end surface on which the light beam is incident. The plug is attached to an incidence end portion of the optical fiber in an arrangement in which the burr defect is located in a short axis direction of a cross section on the incidence end surface of the light beam incident on the incidence end surface in a state in which the plug is engaged with the receptacle.

The "burr defect" means a defect formed on the cut surface when cutting the optical fiber, that is, a burr and a burr defect. A burr is an unnecessary protruding portion remaining on the cut surface, and a burr defect is a defect portion corresponding to a burr on a facing cut surface.

In the optical fiber cable of the present invention, it is preferable that the plug has a positioning structure for positioning of the burr defect and that the burr defect is disposed at a position determined in advance in a relationship with the positioning structure.

In the optical fiber cable of the present invention, it is preferable that the plug includes a holding member that has a cylindrical shape having a through hole and that holds the incidence end portion in the through hole and that the positioning structure is configured to include at least one of a protruding portion, a groove portion, or a flat portion having a surface parallel to a central axis of the optical fiber, all of the protruding portion, the groove portion, and the flat portion being formed on a surface of the holding member.

In the optical fiber cable of the present invention, it is preferable that the positioning structure includes the protruding portion or the groove portion and that the position determined in advance is a position on a first straight line, which passes through the protruding portion or the groove portion and the central axis, or a position on a straight line, which is perpendicular to the first straight line, in a front view of the holding member.

In the optical fiber cable of the present invention, it is preferable that the positioning structure includes the flat portion and that the position determined in advance is a position on a second straight line, which passes through the central axis and is perpendicular to a line formed by the flat portion, or a position on a straight line, which is perpendicular to the second straight line, in a front view of the holding member.

In the optical fiber cable of the present invention, it is preferable that the positioning structure is formed in vicinity of an opening of the through hole and/or on an outer peripheral surface of the holding member.

In the optical fiber cable of the present invention, it is preferable that the holding member has an air gap structure that forms an air gap extending in at least a long axis direction of the cross section on the incidence end surface from an opening position of the through hole. In this case, it is preferable that the air gap extends up to an outer peripheral surface such that the incidence end portion is viewable in a side view of the holding member.

In the optical fiber cable of the present invention, it is preferable that the plug has a housing member that holds the holding member while maintaining an arrangement of the burr defect with respect to the cross section on the incidence end surface.

In the optical fiber cable of the present invention, it is preferable to further comprise: an insert that is provided on an emission end surface side of the optical fiber and that is inserted into a subject; and a light absorption member disposed at a position where the light beam emitted from the emission end surface is emitted. In this case, the insert can be a needle that is inserted into a subject.

A method of manufacturing an optical fiber cable of the present invention includes: preparing a plug, which is engaged with a receptacle for light emission of a light source unit that emits a light beam having a flat-shaped cross section, and an optical fiber having a burr defect in a part of an outer peripheral portion of an incidence end surface on which the light beam is incident; and attaching the plug to an incidence end portion of the optical fiber in an arrangement in which the burr defect is located in a short axis direction of a cross section on the incidence end surface of the light beam incident on the incidence end surface in a state in which the plug is engaged with the receptacle.

In the method of manufacturing an optical fiber cable of the present invention, it is preferable that the plug has a positioning structure for positioning of the burr defect and that the burr defect is disposed at a position, which is determined in advance in a relationship with the positioning structure, by adjusting an arrangement of the plug and/or the optical fiber before attaching the plug to the optical fiber.

In the method of manufacturing an optical fiber cable of the present invention, it is preferable that the plug includes a holding member that has a cylindrical shape having a through hole and that holds the incidence end portion in the through hole and that the positioning structure is configured to include at least one of a protruding portion, a groove portion, or a flat portion having a surface parallel to a central axis of the optical fiber, all of the protruding portion, the groove portion, and the flat portion being formed on a surface of the holding member.

A light source module of the present invention comprises: the optical fiber cable described above; a light source that emits a light beam having a flat-shaped cross section; and a receptacle that is engaged with the plug of the optical fiber cable in order to make the light beam, which is emitted from the light source, incident on the incidence end surface of the optical fiber.

In the light source module of the present invention, it is preferable to further comprise an optical system that condenses the light beam emitted from the light source onto the incidence end surface.

In the light source module of the present invention, it is preferable that a long axis diameter of the cross section on the incidence end surface is equal to or greater than $1/3$ of a diameter of the incidence end surface.

For the optical fiber cable, the method of manufacturing the same, and the light source module comprising the same, it is possible to manufacture the optical fiber cable at lower cost.

BRIEF DESCRIPTION OF THE DRAWINGS

FIG. 18 is a flowchart showing the procedure of generating a photoacoustic image using the photoacoustic image generation apparatus shown in FIG. 15.

DESCRIPTION OF THE PREFERRED EMBODIMENTS

Hereinafter, embodiments of the present invention will be described with reference to the accompanying diagrams. However, the present invention is not limited to these. In addition, the scale of each component is appropriately adjusted in order to have a recognizable size in the diagrams described below.

First Embodiment

Figure 1A:
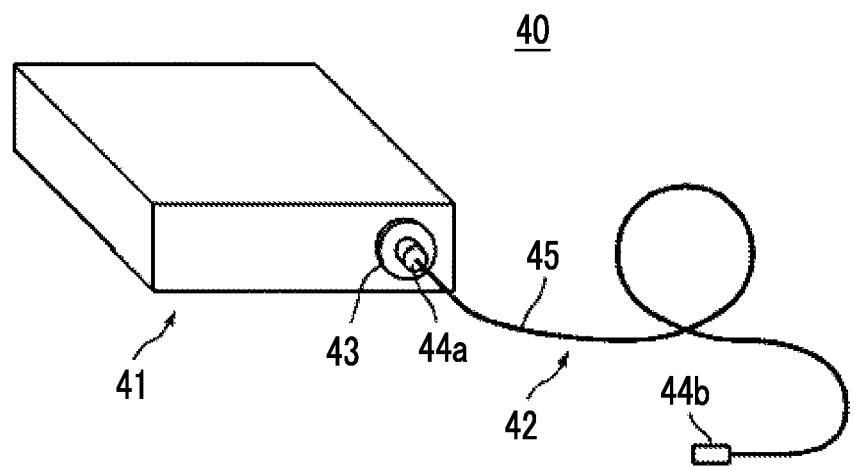
FIG. 1A is a perspective view schematically showing a light source module according to a first embodiment.
Figure 1B:
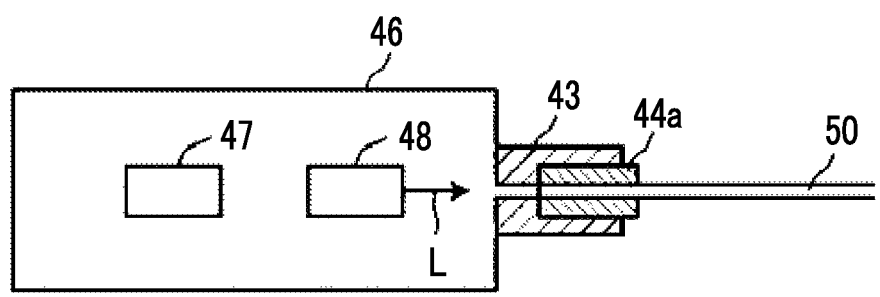
FIG. 1B is a cross-sectional view schematically showing the light source module according to the first embodiment.

First, a first embodiment of the present invention will be described. FIG. 1A is a perspective view schematically showing a light source module according to a first embodiment, and FIG. 1B is a cross-sectional view of the light source module. In this specification, the cross-sectional view shows a cross section in a plane parallel to the plane of paper passing through the central axis of the optical fiber or the cylindrical shape.

As shown in FIGS. 1A and 1B, a light source module 40 according to the present embodiment is configured to include a light source unit 41 and an optical fiber cable 42.

The light source unit 41 has, for example, a receptacle 43, a light source 48, and a driving circuit 47 for the light source 48. The receptacle 43 is attached to the light emitting port of a housing 46, and the light source 48 and the driving circuit 47 are provided inside the housing 46. The outer size of the housing 46 is 74 mm (length)×54 mm (width)×20 mm (height), for example.

The light source 48 is a light source that emits light having a flat-shaped beam cross section (hereinafter, simply referred to as a flat-shaped light). The light source 48 is, for example, a single light emitting element that generates flat-shaped light itself, and a semiconductor laser light source can be mentioned as an example of such a light source. The light source 48 is a light source system including an optical system and a light emitting element, and may form the shape of a beam cross section in a flat shape by the optical system. As examples of such a light source, a combination of a semiconductor laser light source, a solid state laser light source or a gas laser light source, and an optical system for forming the shape of the beam cross section of laser light in a flat shape can be mentioned. The light source system may include an optical amplifier and a wavelength converter. In the present embodiment, as an example, the light source 48 is a semiconductor laser diode. Although not particularly limited, the oblateness $(a-b)/a$ of the beam cross section assuming that the long axis radius and the short axis radius of the beam cross section are a and b, respectively, is 0.5 or more, for example. When a region where burr defects, which will be described later, are formed on the incidence end surface of the optical fiber is taken into consideration, the present invention is particularly effective in a case where the short axis diameter of the beam cross section is smaller than $1/3$ of the diameter of the optical fiber incidence end surface and the long axis diameter of the beam cross section is equal to or greater than $1/3$ of the diameter of the optical fiber incidence end surface. It is preferable that the light is laser light beam. For example, the light is pulsed laser light having a pulse width of 5 ns to 100 ns and a repetition frequency of 2 Hz to 4000 Hz. The wavelength of light is 700 nm to 1100 nm, preferably, 750 nm to 950 nm. The energy density of the light is preferably 0.03 μJ to 50 μJ, more preferably, 0.1 μJ to 20 μJ. For example, laser light of 6 μJ is used.

The optical fiber cable 42 is configured to include a cord portion 45 having an incidence end portion and an emission end portion of light, a plug 44a provided in the incidence end portion, and a plug 44b provided in the emission end portion, for example. The plug 44a has a structure engaged with the receptacle 43, and the optical fiber cable 42 is detachable and attachable from and to the light source unit 41 by a connector structure configured to include the plug 44a and the receptacle 43. For example, the cord portion 45 includes an optical fiber 50, which is configured to include a core and a cladding, and also has a coating layer or the skin (sheath) that covers the optical fiber 50. In the present embodiment, the plug 44a is formed of a ferrule as a holding member for holding the bare optical fiber 50. On the other hand, the plug 44b is not particularly limited, and may be formed of only the ferrule similar to the plug 44a, or may be a plug having other structures (for example, an SC type connector structure, an FC type connector structure, an MU type connector structure, a DS type connector structure, and a DL type connector structure conforming to JIS standards and an ST type connector structure, an LC type connector structure, and an MTRJ type connector structure conforming to IEC standards).

Figure 2A:
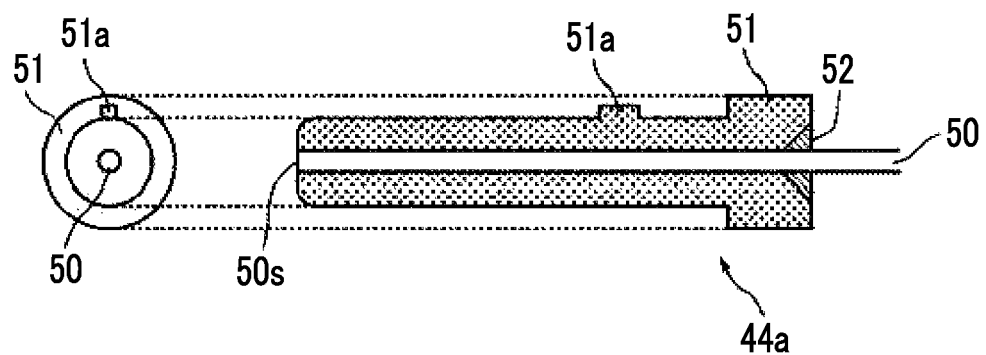
FIG. 2A is a front view and a cross-sectional view schematically showing an incidence end side plug of the optical fiber cable shown in FIGS. 1A and 1B.

FIG. 2A is a front view and a cross-sectional view schematically showing an incidence end side plug of the optical fiber cable shown in FIGS. 1A and 1B. As described above, the optical fiber cable 42 according to the present embodiment is configured to include the optical fiber 50 and a ferrule 51 as the plug 44a.

The optical fiber 50 is not particularly limited, and is a quarts fiber configured to include a common core and cladding, for example. The optical fiber 50 may be a single-mode fiber or a multi-mode fiber. The outer diameter of the optical fiber is 80 μm to 200 μm, for example. In the present invention, an optical fiber having a burr defect of a burr 53a (refer to FIG. 2B) or a burr defect 53b (refer to the FIG. 2C) in a part of the outer peripheral portion of the incidence end surface is used. That is, the optical fiber cable of the present invention is manufactured using the optical fiber 50 with a burr defect since polishing processing for removing the burr defect is not performed even if the burr defect is generated on the cut surface by the cutting of the optical fiber (refer to FIGS. 2B and 2C). Usually, a burr defect is formed in the outer peripheral portion of the cut surface when damage to the optical fiber surface is given and bending stress is applied to cut (so-called cleave cut) the optical fiber surface. Usually, when the burr 53a is formed on one of two cut surfaces, a burr defect is formed on the other cut surface 50s. The burr 53a and the burr defect 53b have shapes complementary to each other. The range in which the burr defect is formed is usually a range from the outer periphery to a distance of ⅓ of the diameter of the optical fiber at the maximum, and may be formed not only in a part of a region of a cladding 50b but also in a part of a region including a core 50a and the cladding 50b.

The ferrule 51 has an approximately cylindrical shape having a through hole, the diameter of the through hole (that is, the inner diameter of the ferrule) is, for example, 80 μm to 200 μm, and the outer diameter (maximum size in a direction perpendicular to the central axis) of the ferrule is, for example, 1.5 mm to 5 mm. The material of the ferrule 51 is not particularly limited, and metal materials, ceramic materials, plastic materials, and glass materials that are commonly used can be used. For example, these are stainless steel, zirconia ceramics, and engineering plastics for resin molding. In addition, for example, in the ferrule 51, curvature is given to a connection portion between the incidence end surface and the outer peripheral surface, and a flange portion is formed on the emission end surface side. The incidence end surface of the ferrule is assumed to be a surface that can be checked mainly in a front view of the ferrule (excluding a surface that is physically separated, such as a flange portion; the same hereinbelow), and the emission end surface of the ferrule is assumed to be a surface that can be checked mainly in a rear view of the ferrule. In addition, the outer peripheral surface of the ferrule is assumed to be a portion excluding the incidence end surface and the emission end surface of the surface of the ferrule. The flange portion may be formed integrally with a cylindrical portion, or may be separately formed after forming the cylindrical portion. In addition, there may be no flange portion. In the ferrule 51, a protruding portion 51a as a positioning structure that is a reference (or a mark) for relative positioning of a burr defect is provided on the outer peripheral surface. The "positioning" is a meaning including "determining the position of the burr defect in a direction along the central axis of the ferrule 51" and "determining the angle of the burr defect around the central axis by rotating the optical fiber". The size (width or height in a front view in FIG. 2A) of the protruding portion 51a is not particularly limited. In the case of performing the positioning of the burr defect for the ferrule 51, the size of the protruding portion 51a may be any size that can be checked by visual observation (including a case where the magnifying glass, such as a microscope, is used) in a front view and that functions as an alignment structure when the plug and the receptacle are engaged with each other. For example, it is preferable that the size of the protruding portion 51a is 0.3 mm to 1.0 mm in width and 0.3 mm to 1.0 mm in height. The alignment structure is a structure to engage the plug with the receptacle in a specific relative arrangement.

In the present embodiment, in a case where light emitted from the light source 48 is incident on the incidence end surface 50s in a state in which the ferrule 51 (plug 44a) is engaged with the receptacle 43, the ferrule 51 (plug 44a) is attached to an end portion of the optical fiber 50 on the incidence end surface 50s side in an arrangement in which a burr defect is located in the short axis direction of the beam cross section on the incidence end surface 50s. The ferrule 51 and the optical fiber 50 are fixed to each other, for example, by an adhesive 52. The step of attaching the ferrule 51 to the optical fiber 50 includes, for example, a step of inserting the optical fiber 50 into the through hole of the ferrule 51 and a step of adjusting the arrangement of the optical fiber 50 by rotating or moving the optical fiber 50 back and forth within the through hole while checking the incidence end surface using a microscope so that the burr defect is disposed at a position determined in advance in the relationship with the protruding portion 51a (positioning structure) in consideration of the short axis direction of the beam cross section. For example, in the present embodiment, the burr defect is disposed at the lowermost position in FIGS. 2A to 2C.

Figure 3:
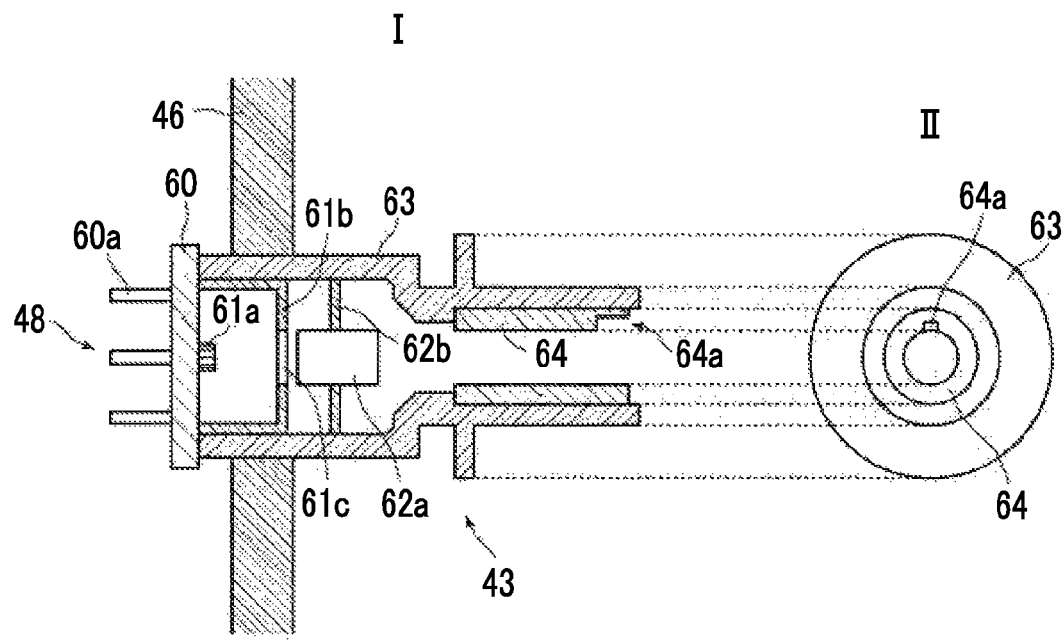
FIG. 3 is a cross-sectional view I and a front view II schematically showing a receptacle for light emission of the light source unit shown in FIGS. 1A and 1B.

FIG. 3 is a cross-sectional view I and a front view II schematically showing a receptacle for light emission of the light source unit shown in FIGS. 1A and 1B.

For example, the receptacle 43 has an approximately cylindrical shell 63 provided in the opening for light emission of the housing 46, a sleeve 64 provided on the inner wall of the shell 63 on a side where the ferrule 51 is inserted, and a lens 62a for condensing laser light L emitted from the light source onto the incidence end surface 50s of the optical fiber 50. The sleeve 64 has an inner diameter that is approximately the same as the outer diameter of an insertion portion of the ferrule 51. Accordingly, in a case where the ferrule 51 is inserted into the receptacle 43, the insertion portion of the ferrule 51 is held in the sleeve 64. In addition, the sleeve 64 has a notch 64a fitted to the protruding portion 51a of the ferrule 51. Accordingly, the protruding portion 51a and the notch 64a form the alignment structure of the ferrule 51 and the receptacle 43. The lens 62a is disposed at a position where the laser light L is condensed onto the incidence end surface 50s in a state in which the ferrule 51 is engaged with the receptacle 43. The lens 62a is not particularly limited, and is a SELFOC (registered trademark) microlens (self-focus-forming type rod lens in which the refractive index changes in the radial direction), for example.

In addition, a semiconductor laser diode (LD) as the light source 48 is provided in the opening of the shell 63 on a side opposite to the side where the ferrule 51 is inserted. The LD includes a stem 60, a semiconductor light emitting element 61a provided on the stem 60 and a cap 61b with a glass window 61c, which is provided on the stem 60 so as to cover the semiconductor light emitting element 61a. The LD is fixed to the receptacle 43 by the cap 61b being fitted into the receptacle 43 (shell 63). At this time, the short axis direction of the laser light L on the incidence end surface of the optical fiber 50 is designed to be a specific direction. For example, in the present embodiment, the short axis direction is designed to be a vertical direction in FIG. 3. A lead terminal 60a is provided in the stem 60, and the lead terminal 60a is electrically connected to the driving circuit 47 for the LD.

Figure 2B:
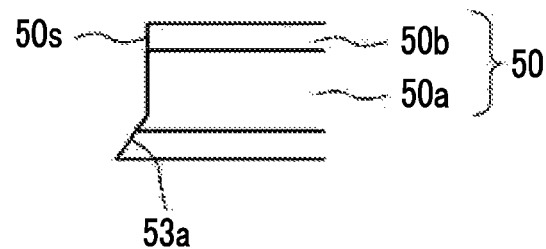
FIG. 2B is a cross-sectional view of an incidence end portion of an optical fiber that schematically shows an example of a burr defect.
Figure 2C:
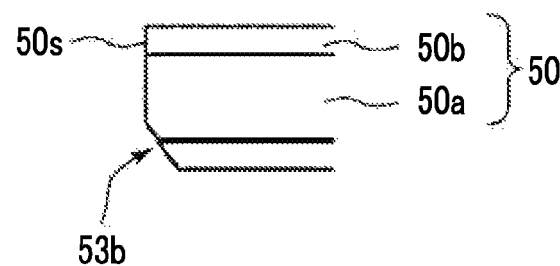
FIG. 2C is a cross-sectional view of an incidence end portion of an optical fiber that schematically shows an example of a burr defect.
Figure 4:
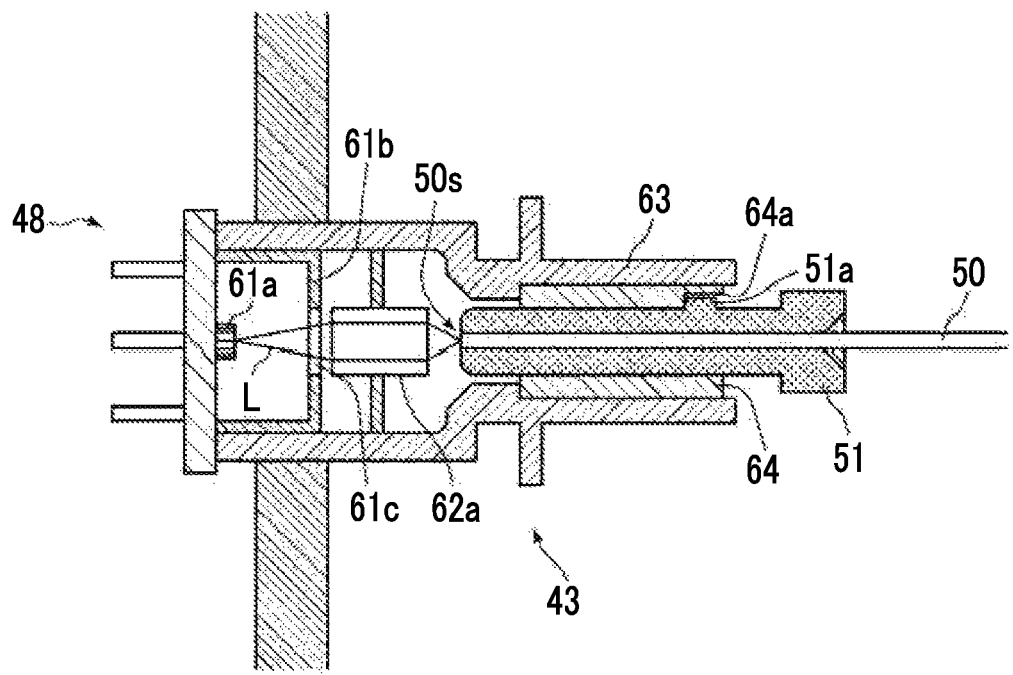
FIG. 4 is a cross-sectional view schematically showing a state in which the plug shown in FIGS. 2A to 2C is connected to the receptacle shown in FIG. 3 by being inserted thereinto.
Figure 5:
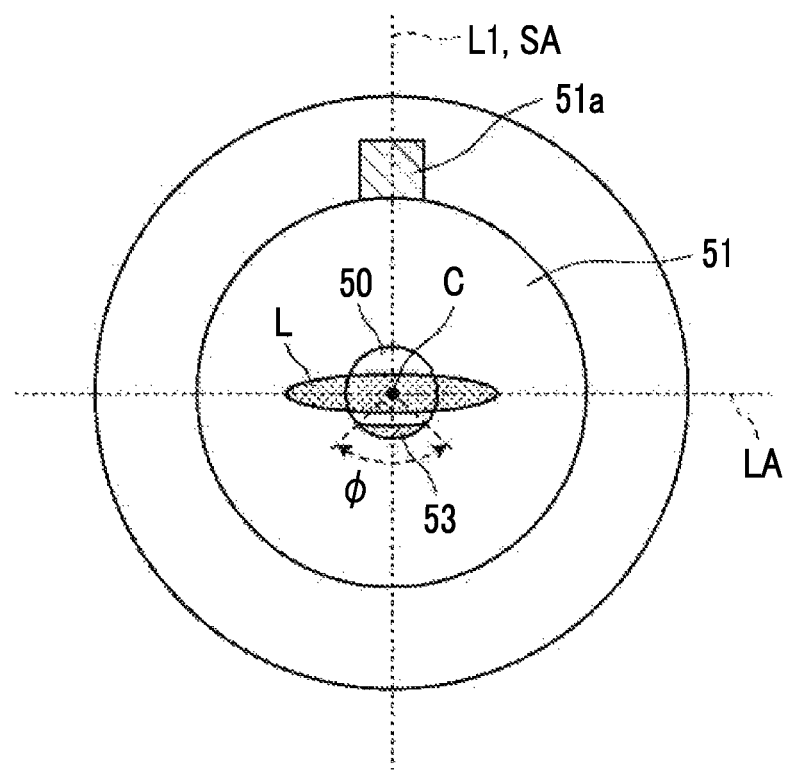
FIG. 5 is a diagram schematically showing how light having a flat-shaped cross section is incident from the incidence end surface of the optical fiber in the first embodiment.

FIG. 4 is a cross-sectional view schematically showing a state in which the plug shown in FIGS. 2A to 2C is connected to the receptacle shown in FIG. 3 by being inserted thereinto. FIG. 5 is a diagram schematically showing how flat-shaped light is incident from the incidence end surface of the optical fiber in the present embodiment. As shown in FIG. 4, the ferrule 51 is connected to the receptacle 43 by being inserted thereinto so that the protruding portion 51a is fitted into the notch 64a of the sleeve 64. When the flat-shaped laser light L is emitted from the semiconductor light emitting element 61a in a state in which the ferrule 51 is connected to the receptacle 43, the laser light L is condensed by the lens 62a provided in the cap 61b, and the condensed laser light L is incident from the incidence end surface of the optical fiber 50.

The effect of the present invention will be described below. In the present embodiment, as described above, a burr defect 53 is disposed at the lowermost position in FIGS. 2A to 2C or FIG. 5. That is, it can be said that the burr defect 53 is disposed on a straight line L1, which passes through the central axis C of the optical fiber 50 and the protruding portion 51a, in a front view of the ferrule 51. Alternatively, it can be said that there is a "relationship that the angle between a line connecting the protruding portion 51a to the central axis C and a line connecting the central axis C to the burr defect 53 is 180°" between the burr defect 53 and the protruding portion 51a. As described above, a short axis direction SA of the laser light L on the incidence end surface of the optical fiber 50 is designed to be a vertical direction in FIG. 5, and a long axis direction LA thereof is designed to be a horizontal direction in FIG. 5. As a result, since the burr defect 53 is located in the short axis direction SA with respect to the central axis C, it is possible to avoid a situation in which a region on which the laser light L is incident overlaps a region where the burr defect 53 is present. That is, even if the burr defect 53 is formed in the region of the core 50a, it is possible to make the flat-shaped laser light L incident on the core 50a of the optical fiber 50 without being influenced by the burr defect 53. The burr defect 53 is "located in the short axis direction" means that the burr defect is disposed at a position, which is included in the angle range of 120° (reference numeral φ in FIG. 5) around the short axis direction, in a front view of the ferrule 51 (plug).

As described above, according to the optical fiber cable and the light source module of the present invention, it is possible to suppress the energy loss of laser light due to a burr defect even if the optical fiber with burr defect is used in a situation where a semiconductor laser light source, which generates flat-shaped laser light theoretically, is used or a situation where laser light whose beam cross section is formed in a flat shape is used. Thus, since it is possible to use the optical fiber with burr defect regardless of whether or not the burr defect is formed in the region of the core, polishing processing for removing the burr defect, which is essential in the related art, is not required in the optical fiber manufacturing step. This means that it is possible to reduce the cost for manufacturing the optical fiber by the number of steps reduced compared with the related art. As a result, according to the optical fiber cable, the method for manufacturing the same, and the light source module including the same of the present invention, it is possible to manufacture the optical fiber cable and the light source module at lower cost than in the related art.

In the explanation of the first embodiment, in FIG. 5, the case has been described in which the burr defect 53 is disposed at the lowermost position and the short axis direction SA of the laser light L is a vertical direction. However, the present invention is not limited thereto. For example, FIGS. 6A to 6C are diagrams schematically showing other examples of the positional relationship between the protruding portion 51a, which is a positioning structure, and the burr defect 53 in the first embodiment.

Figure 6A:
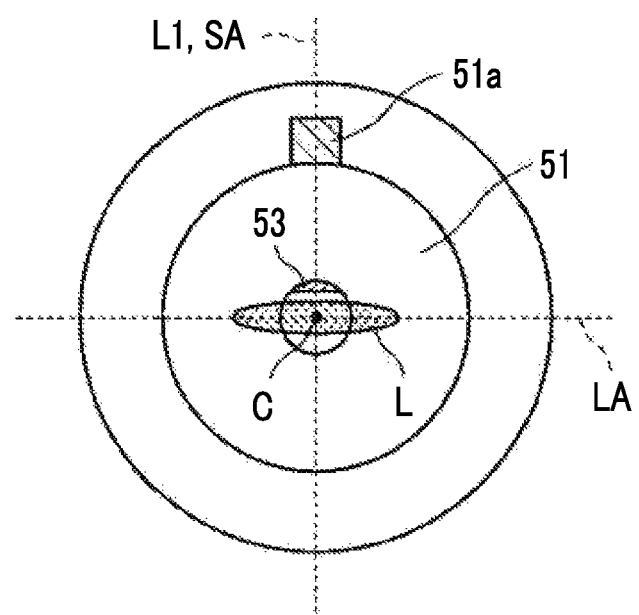
FIG. 6A is a diagram schematically showing another example of the positional relationship between a positioning structure and a burr defect in the first embodiment.

FIG. 6A shows an arrangement in a case where the burr defect 53 is disposed at the uppermost position and the short axis direction SA of the laser light L is a vertical direction. Also in this case, it can be said that the burr defect 53 is disposed on the straight line L1, which passes through the central axis C of the optical fiber 50 and the protruding portion 51a, in a front view of the ferrule 51. Alternatively, it can be said that there is a "relationship that the angle between a line connecting the protruding portion 51a to the central axis C and a line connecting the central axis C to the burr defect 53 is 0°" between the burr defect 53 and the protruding portion 51a. Thus, in a case where the short axis direction SA of the laser light L is designed to be a vertical direction, even if the burr defect 53 is disposed on the upper side, it is possible to avoid a situation in which a region on which the laser light L is incident overlaps a region where the burr defect 53 is present.

Figure 6B:
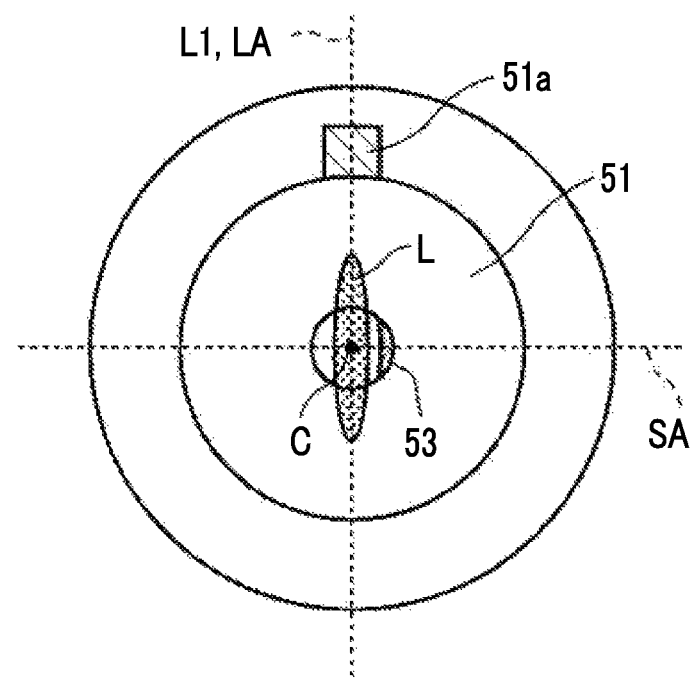
FIG. 6B is a diagram schematically showing another example of the positional relationship between a positioning structure and a burr defect in the first embodiment.

FIG. 6B shows an arrangement in a case where the burr defect 53 is disposed at the rightmost position and the short axis direction SA of the laser light L is a horizontal direction. That is, it can be said that the burr defect 53 is disposed on a straight line perpendicular to the straight line L1, which passes through the central axis C of the optical fiber 50 and the protruding portion 51a, in a front view of the ferrule 51. Alternatively, it can be said that there is a "relationship that the angle between a line connecting the protruding portion 51a to the central axis C and a line connecting the central axis C to the burr defect 53 is 90°" between the burr defect 53 and the protruding portion 51a. Thus, in a case where the short axis direction SA of the laser light L is designed to be a horizontal direction, if the burr defect 53 is disposed on the right side, it is possible to avoid a situation in which a region on which the laser light L is incident overlaps a region where the burr defect 53 is present. In addition, in the above case, the same effect is obtained even if the burr defect 53 is disposed on the left side.

Figure 6C:
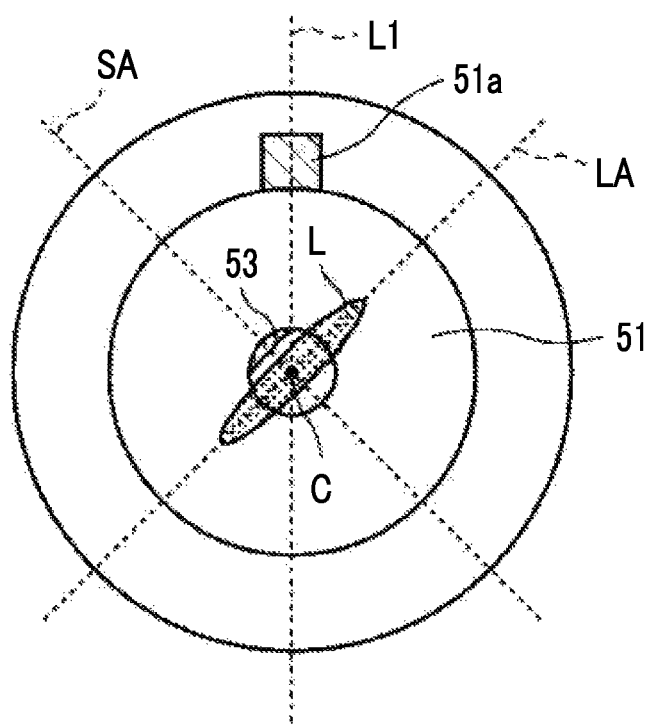
FIG. 6C is a diagram schematically showing another example of the positional relationship between a positioning structure and a burr defect in the first embodiment.

FIG. 6C shows an arrangement in a case where the burr defect 53 is disposed at the left-diagonal upper position and the short axis direction SA of the laser light L is inclined by 45° to the left from the vertical direction (state in FIG. 6A). That is, it can be said that there is a "relationship that the angle between the line connecting the protruding portion 51a to the central axis C and the line connecting the central axis C to the burr defect 53 is 45° to the left" between the burr defect 53 and the protruding portion 51a. Thus, the burr defect 53 may be disposed so as to be located in the short axis direction from the central axis C in a front view. The positional relationship between the burr defect 53 and the protruding portion 51a is determined depending on an arbitrary specific direction that is the short axis direction SA of the laser light L. Also in the case shown in FIG. 6C, it is possible to avoid a situation in which a region on which the laser light L is incident overlaps a region where the burr defect 53 is present. In the above case, the same effect is obtained even if the burr defect 53 is disposed at a position where the angle between the two line segments described above is 135° to the right side.

In the explanation of the first embodiment, a single-core optical fiber cable has been described. However, in the present invention, a multi-core optical fiber cable may be used. For example, in the multi-core optical fiber cable, one protruding portion is provided as a positioning structure in the ferrule, and the arrangement of each core wire fiber (that is, arrangement of the burr defect) is determined so as to have a predetermined positional relationship with the one protruding portion (that is, a relationship that the burr defect is located in the short axis direction of the beam cross section on the incidence end surface) in consideration of the short axis direction of laser light. Alternatively, a plurality of protruding portions as positioning structures are provided in the ferrule so as to correspond to respective core wire fibers, and the arrangement of the respective core wire fibers is determined as to have a predetermined positional relationship with each corresponding protruding portion in consideration of the short axis direction of laser light. In the multi-core optical fiber cable, the arrangement of the core wire fiber may be different for each core wire fiber.

Second Embodiment

Figure 7:
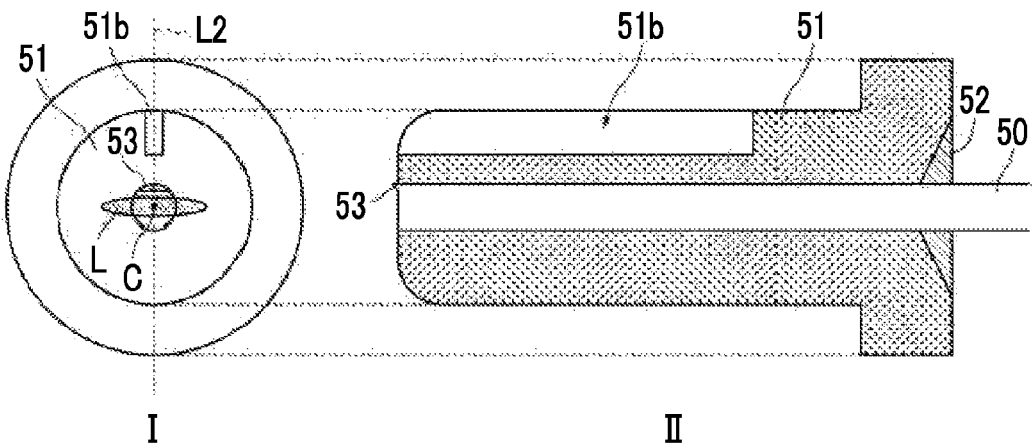
FIG. 7 is a front view I and a cross-sectional view II schematically showing a plug of an optical fiber cable according to a second embodiment.

Next, a second embodiment of the present invention will be described. FIG. 7 is a front view I and a cross-sectional view II schematically showing a plug of an optical fiber cable according to the second embodiment.

A light source module according to the present embodiment is different from the light source module according to the first embodiment mainly in that a groove portion is used in the alignment structure of a plug and a receptacle and the positioning structure of a plug. Accordingly, the same reference numerals are given to the same components as in the first embodiment, and the detailed explanations thereof will be omitted as long as there is no particular need.

The plug according to the present embodiment is also formed by the ferrule 51. The optical fiber 50 is inserted into the through hole of the ferrule 51, and the optical fiber 50 is fixed to the ferrule 51 by the adhesive 52. The ferrule 51 according to the present embodiment has a groove portion 51b as a positioning structure.

The groove portion 51b is formed in a notch shape having a length along the central axis C. An opening of the groove portion 51b is also formed on the incidence end surface of the ferrule 51. Therefore, also in a front view, it is possible to visually check the opening of the groove portion 51b. The size (width or height in a front view of I of FIG. 7) of the groove portion 51b is not particularly limited. In the case of performing the positioning of the burr defect for the ferrule 51, the size of the groove portion 51b may be any size that can be checked by visual observation in a front view and that functions as an alignment structure of the plug and the receptacle. For example, the size of the groove portion 51b is 0.5 mm to 1.0 mm in width and 0.2 mm to 1.0 mm in height. The groove portion may also be a tapered structure in which the position of the ferrule is fixed as the ferrule is inserted. As such a tapered structure, for example, it is possible to adopt a structure in which the width and/or the height of a groove portion continuously decreases toward the back surface from the front surface (from left to right in II of FIG. 7) back. In the receptacle according to the present embodiment, a protruding portion (not shown) fitted into the groove portion 51b when the ferrule 51 is inserted into the receptacle is formed on the sleeve. That is, the groove portion 51b has a guide function of the protruding portion of the sleeve, and also forms an alignment structure of the ferrule 51 and the receptacle.

As shown in I of FIG. 7, the burr defect 53 is disposed on a straight line L2, which passes through the central axis C of the optical fiber 50 and the groove portion 51b, in a front view of the ferrule 51, for example. That is, the angle between the line connecting the groove portion 51b to the central axis C and the line connecting the central axis C to the burr defect 53 is 0°. On the other hand, the short axis direction of the laser light L is a vertical direction in FIG. 7 as in the first embodiment.

As described above, also in the light source module according to the present embodiment, it is possible to perform the positioning of the burr defect so that the groove portion 51b as a positioning structure and the burr defect have a predetermined positional relationship therebetween in consideration of the short axis direction of laser light. As a result, since it is possible to avoid a situation in which a region on which the laser light L is incident overlaps a region where the burr defect 53 is present, the same effect as in the first embodiment is obtained.

Third Embodiment

Figure 8A:
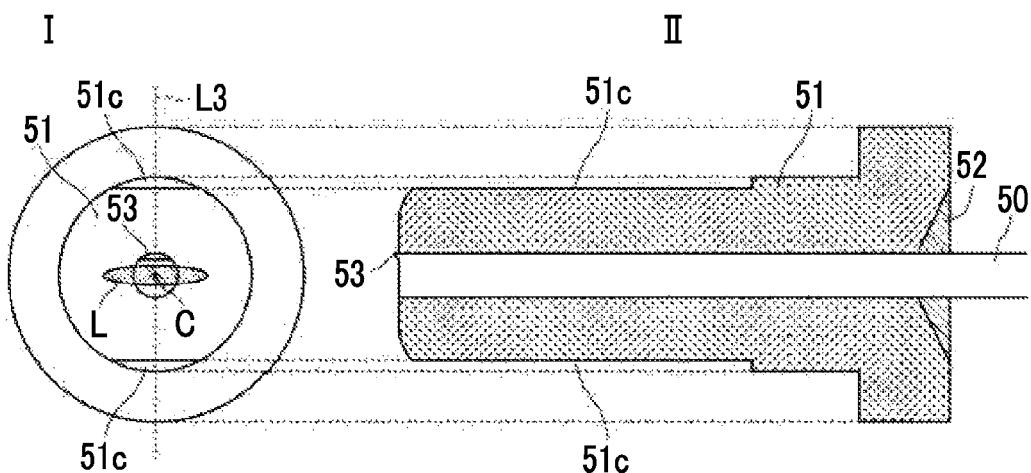
FIG. 8A is a front view I and a cross-sectional view II schematically showing a plug of an optical fiber cable according to a third embodiment.
Figure 8B:
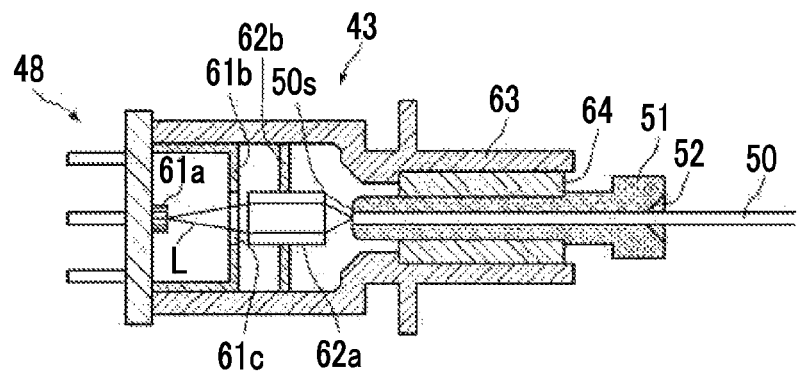
FIG. 8B is a cross-sectional view schematically showing a state in which the plug according to the third embodiment is connected to a receptacle corresponding thereto by being inserted into the receptacle.

Next, a third embodiment of the present invention will be described. I of FIG. 8A is a front view schematically showing a plug of an optical fiber cable according to the third embodiment, and II of FIG. 8A is a cross-sectional view of I of FIG. 8A. FIG. 8B is a cross-sectional view schematically showing a state in which the plug according to the third embodiment is connected to a receptacle corresponding thereto by being inserted into the receptacle.

A light source module according to the present embodiment is different from the light source module according to the first embodiment mainly in that a flat portion having a surface parallel to the central axis is used in the alignment structure of a plug and a receptacle and the positioning structure of a plug. Accordingly, the same reference numerals are given to the same components as in the first embodiment, and the detailed explanations thereof will be omitted as long as there is no particular need.

The plug according to the present embodiment is also formed by the ferrule 51. The optical fiber 50 is inserted into the through hole of the ferrule 51, and the optical fiber 50 is fixed to the ferrule 51 by the adhesive 52. The ferrule 51 according to the present embodiment has a flat portion 51c having a surface parallel to the central axis as a positioning structure.

As shown in I of FIG. 8A, the flat portion 51c is a peripheral surface portion having a surface parallel to the central axis C, and two flat portions 51c are formed on the upper and lower sides so as to face each other with the central axis interposed therebetween. The flat surfaces of the two flat portions 51c are parallel to each other. The flat portions 51c reach the incidence end surface of the ferrule 51, and the flat surface of each flat portion 51c appears as a boundary line of a step difference in a front view (refer to I of FIG. 8A). The depth (distance to the boundary line from the outer peripheral line of the ferrule 51 on a line L3 that passes through the central axis C and is perpendicular to the boundary line in a front view of I of FIG. 8A) of each flat portion 51c is not particularly limited. In the case of performing the positioning of the burr defect for the ferrule 51, the depth of each flat portion 51c may be any size at which the difference between the outer peripheral line of the ferrule 51 and the boundary line can be checked by visual observation in a front view and which functions as an alignment structure of the plug and the receptacle. For example, the depth of each flat portion 51c is 0.1 mm to 0.5 mm. A sleeve provided in the receptacle according to the present embodiment has an opening with the same shape as a cross-sectional shape perpendicular to the central axis of a cylindrical portion in which the flat portion 51c is formed. That is, the sleeve has a flat portion, which is complementary to the flat portion 51c, on the upper and lower sides of the inner hole. When the ferrule 51 is inserted into the receptacle, the flat portion 51c slides while facing the flat portion of the sleeve so as to be close thereto (refer to the FIG. 8B). Accordingly, the flat portion 51c and the flat portion of the sleeve form the alignment structure of the ferrule 51 and the receptacle.

As shown in I of FIG. 8A, the burr defect 53 is disposed on the straight line L3 perpendicular to the boundary line, which passes through the central axis C of the optical fiber 50 and which is formed by the flat portion 51c, in a front view of the ferrule 51, for example. That is, the angle between the line perpendicular to the boundary line passing through the central axis C and the line connecting the central axis C to the burr defect 53 is 0°. On the other hand, the short axis direction of the laser light L is a vertical direction in FIG. 8 as in the first embodiment.

As described above, also in the light source module according to the present embodiment, it is possible to perform the positioning of the burr defect so that the flat portion 51c as a positioning structure and the burr defect have a predetermined positional relationship therebetween in consideration of the short axis direction of laser light. As a result, since it is possible to avoid a situation in which a region on which the laser light L is incident overlaps a region where the burr defect 53 is present, the same effect as in the first embodiment is obtained.

Fourth Embodiment

Figure 9A:
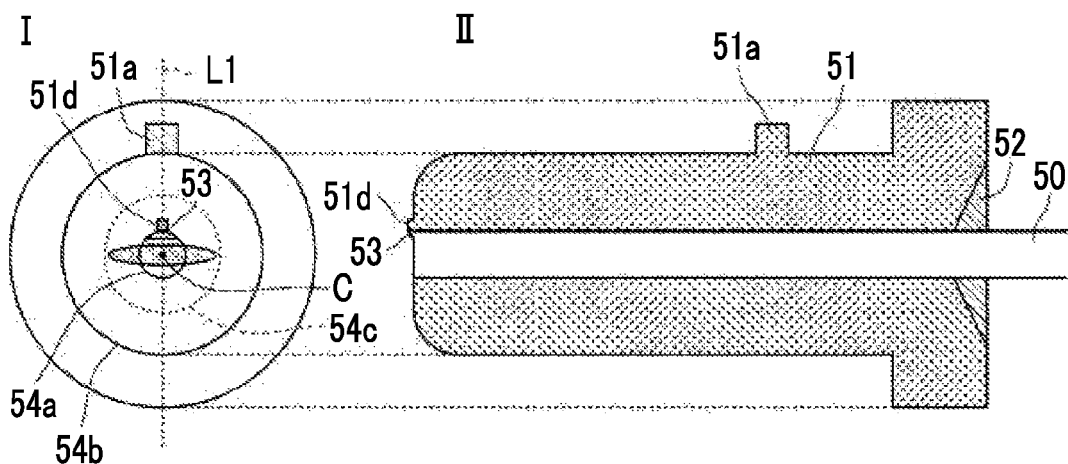
FIG. 9A is a front view I and a cross-sectional view II schematically showing a plug of an optical fiber cable according to a fourth embodiment.
Figure 9B:
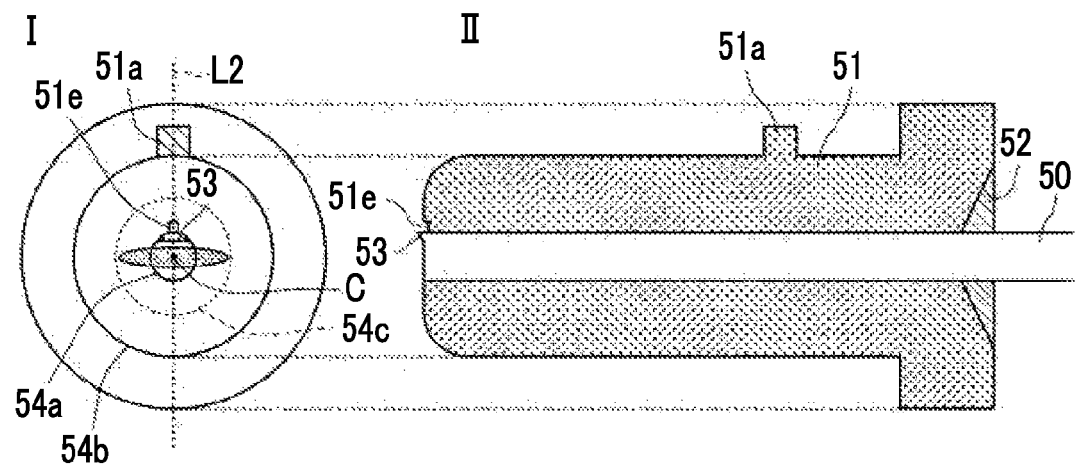
FIG. 9B is a front view I and a cross-sectional view II schematically showing a plug of an optical fiber cable according to the fourth embodiment.

Next, a fourth embodiment of the present invention will be described. FIGS. 9A and 9B are a front view and a cross-sectional view schematically showing a plug of an optical fiber cable according to the fourth embodiment.

A light source module according to the present embodiment is different from the light source module according to the first embodiment mainly in that an element used as an alignment structure is different from an element used as a positioning structure. Accordingly, the same reference numerals are given to the same components as in the first embodiment, and the detailed explanations thereof will be omitted as long as there is no particular need.

The plug according to the present embodiment is also formed by the ferrule 51. The optical fiber 50 is inserted into the through hole of the ferrule 51, and the optical fiber 50 is fixed to the ferrule 51 by the adhesive 52. The ferrule 51 according to the present embodiment has a protruding portion 51d as a positioning structure in addition to the configuration of the ferrule shown in FIGS. 2A to 2C.

As shown in FIG. 9A, the protruding portion 51d is formed at a position adjacent to the upper side of the opening of the through hole of the ferrule 51 in a front view. The size (width or height in a front view of I of FIG. 9A) of the protruding portion 51d is not particularly limited. In the case of performing the positioning of the burr defect for the ferrule 51, the size of the protruding portion 51d may be any size that can be checked by visual observation in a front view. For example, the size of the protruding portion 51d is 0.1 mm to 1.0 mm, preferably 0.2 mm to 0.5 mm. In the present embodiment, it is preferable that the protruding portion 51d functions as a positioning structure (that is, a mark at the time of positioning), and neither the size nor the durability for the protruding portion 51a that functions as an alignment structure is required. Therefore, the protruding portion 51d may be smaller than the protruding portion 51a. In addition, the protruding portion 51d according to the present embodiment may be located in the vicinity of the opening in a range in which the alignment accuracy can be ensured, and does not necessarily need to be adjacent to the opening. The vicinity of the opening is a range closer to the opening than to a middle point 54c between the position of the opening on the outer periphery 54a and the position of the incidence end surface of the ferrule 51 on the outer line 54b, for example, in a front view. That is, the vicinity of the opening is a range surrounded by the circle of reference numeral 54a and the circle of reference numeral 54c in I of FIG. 9A. The sleeve provided in the receptacle according to the present embodiment is the same as that in the first embodiment, and the ferrule 51 and the receptacle according to the present embodiment are also connected as shown in FIG. 4.

As shown in I of FIG. 9A, the burr defect 53 is disposed on a straight line perpendicular to the straight line L1, which passes through the central axis C of the optical fiber 50 and the protruding portion 51d, in a front view of the ferrule 51, for example. That is, the angle between the line connecting the protruding portion 51d to the central axis C and the line connecting the central axis C to the burr defect 53 is 0°. On the other hand, the short axis direction of the laser light L is a vertical direction in I of FIG. 9A as in the first embodiment.

As described above, also in the light source module according to the present embodiment, it is possible to perform the positioning of the burr defect so that the protruding portion 51d as a positioning structure and the burr defect have a predetermined positional relationship therebetween in consideration of the short axis direction of laser light. As a result, since it is possible to avoid a situation in which a region on which the laser light L is incident overlaps a region where the burr defect 53 is present, the same effect as in the first embodiment is obtained.

In the present embodiment, since the protruding portion 51d as a positioning structure is disposed in the vicinity of the opening of the through hole, it is possible to perform the positioning of the burr defect at a position closer than the positioning structure. Therefore, since it becomes easy to adjust the positioning, burr defect arrangement accuracy is improved.

Although the case where the protruding portion 51d is provided in the vicinity of the opening has been described above, the same effect can be obtained even if the protruding portion 51d is replaced with a groove portion 51e as in I and II of FIG. 9B.

Fifth Embodiment

Figure 10A:
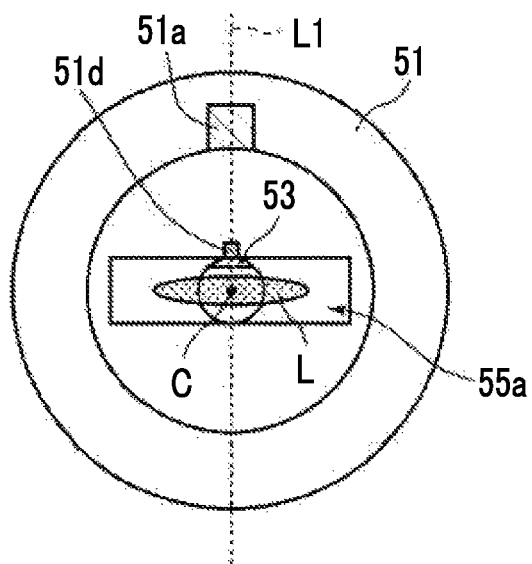
FIG. 10A is a front view schematically showing a plug of an optical fiber cable according to a fifth embodiment.
Figure 10B:
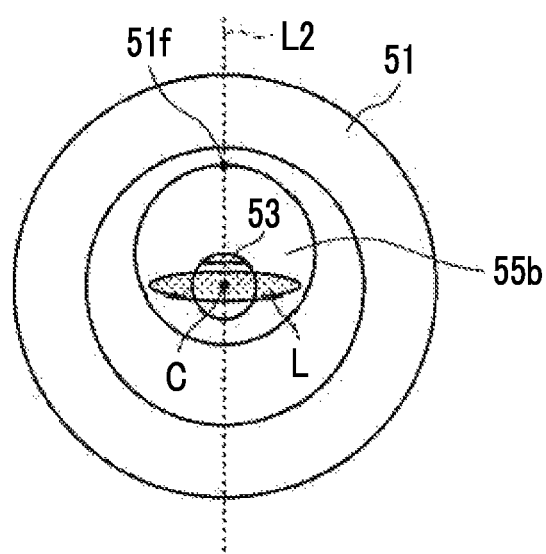
FIG. 10B is a front view schematically showing a plug of an optical fiber cable according to the fifth embodiment.
Figure 10C:
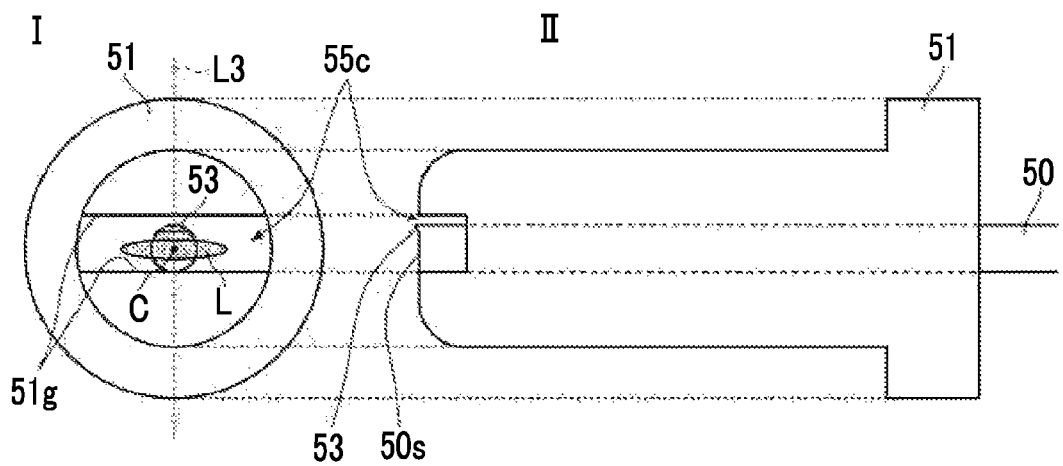
FIG. 10C is a front view I and a side view II schematically showing a plug of an optical fiber cable according to the fifth embodiment.

Next, a fifth embodiment of the present invention will be described. FIGS. 10A to 10C are front views and a side view schematically showing a plug of an optical fiber cable according to a fifth embodiment. The present embodiment is mainly characterized in that an air gap structure for forming an air gap in the vicinity of the incidence end portion of the optical fiber. In addition, in the present embodiment, components of an optical fiber cable other than a ferrule and a receptacle or a light source are the same as those in the first embodiment, for example, unless otherwise specified.

The plug shown in FIG. 10A is also formed by the ferrule 51. The optical fiber 50 is inserted into the through hole of the ferrule 51, and the optical fiber 50 is fixed to the ferrule 51 by the adhesive 52. The ferrule 51 according to the present embodiment has an air gap structure in addition to the configuration of the ferrule in I of FIG. 9A.

The air gap structure is formed by a groove for exposing the side surface near the incidence end surface of the optical fiber 50, and the depth from the incidence end surface is approximately 1 mm to 5 mm, preferably, 1 mm to 3 mm.

The range of the groove may be any range in which the outer edge of an air gap 55a includes the beam cross section on the incidence end surface of the laser light L in a front view of the ferrule 51, and the shape is not particularly limited. The air gap 55a shown in FIG. 10A has a rectangular shape in which a groove having the same width as the diameter of the optical fiber 50 extends along the long axis direction of the laser light L. The length of the groove in the long axis direction is larger than the long axis diameter of the laser light L and is smaller than the diameter of the ferrule 51.

Usually, since laser light is condensed so as to be focused on the incidence end surface of the optical fiber, the energy density of the laser light is increased on the incidence end surface. Therefore, by providing such an air gap structure, it is possible to avoid the emission of laser light to the ferrule in a state in which the energy density is high. As a result, it is possible to prevent the ferrule from being damaged.

The ferrule 51 shown in FIG. 10B is another form of the ferrule having an air gap structure. In the ferrule 51 shown in FIG. 10B, an air gap structure that forms a circular air gap 55b, in which the center of the center is located at a position shifted upward from the central axis C, is formed. Such an air gap 55b can be also used as a groove portion as a positioning structure. For example, in FIG. 10B, using a point 51f on the uppermost side of the outer edge of the air gap 55b as a positioning structure of the burr defect 53, it is possible to arrange the burr defect 53 on the straight line L2 passing through the central axis C of the optical fiber 50 and the point 51f. That is, the angle between the line connecting the point 51f to the central axis C and the line connecting the central axis C to the burr defect 53 is 0°. In a case where the receptacle has a protruding portion that is fitted into the air gap 55b (that is, a groove) and has a shape preventing the rotation of the ferrule, the air gap structure also functions as an alignment structure of the ferrule and the receptacle together with the protruding portion. In addition, without using the air gap structure for alignment, a protrusion or a groove as an alignment structure may be separately provided in the outer peripheral portion of the ferrule.

Also in the light source module described above, it is possible to perform the positioning of the burr defect so that the point 51f as a positioning structure and the burr defect have a predetermined positional relationship therebetween in consideration of the short axis direction of laser light. As a result, since it is possible to avoid a situation in which a region on which the laser light L is incident overlaps a region where the burr defect 53 is present, the same effect as in the first embodiment is obtained.

The ferrule 51 in I of FIG. 10C is also another form of the ferrule having an air gap structure. In the ferrule 51 in I of FIG. 10C, an air gap structure that forms a strip-shaped air gap 55c, in which a groove having a larger width than the diameter of the optical fiber 50 extends along the long axis direction of the laser light L, is formed. In a side view of the ferrule, the air gap 55c extends up to the outer peripheral surface so that the incidence end portion of the optical fiber 50 can be viewed (refer to II of FIG. 10C). Here, "extend up to the outer peripheral surface so that the incidence end portion of the optical fiber 50 can be viewed" means that the air gap is open from the region of the outer peripheral surface so that the incidence end portion of the optical fiber can be viewed without being obstructed by the ferrule in a side view. By providing such an air gap structure, it is possible to check the incidence end surface of the optical fiber from the side view. As a result, it is possible to improve the positioning accuracy of the optical fiber 50 in a direction along the central axis C.

In addition, since the air gap structure shown in I of FIG. 10C include a flat portion 51g having a surface parallel to the central axis, the air gap structure also functions as a positioning structure. That is, in I of FIG. 10C, using the boundary line of the air gap 55c as a reference for the positioning of the burr defect 53, it is possible to arrange the burr defect 53 on the straight line L3 perpendicular to the boundary line passing through the central axis C of the optical fiber 50. That is, the angle between the line perpendicular to the boundary line passing through the central axis C and the line connecting the central axis C to the burr defect 53 is 0°. In a case where the receptacle has a protruding portion that is fitted into the air gap 55c and has a shape preventing the rotation of the ferrule, the air gap structure also functions as an alignment structure of the ferrule and the receptacle together with the protruding portion. In addition, without using the air gap structure for alignment, a protrusion or a groove as an alignment structure may be separately provided in the outer peripheral portion of the ferrule.

Also in the light source module described above, it is possible to perform the positioning of the burr defect so that the flat portion 51g as a positioning structure and the burr defect have a predetermined positional relationship therebetween in consideration of the short axis direction of laser light. As a result, since it is possible to avoid a situation in which a region on which the laser light L is incident overlaps a region where the burr defect 53 is present, the same effect as in the first embodiment is obtained.

Sixth Embodiment

Figure 11A:
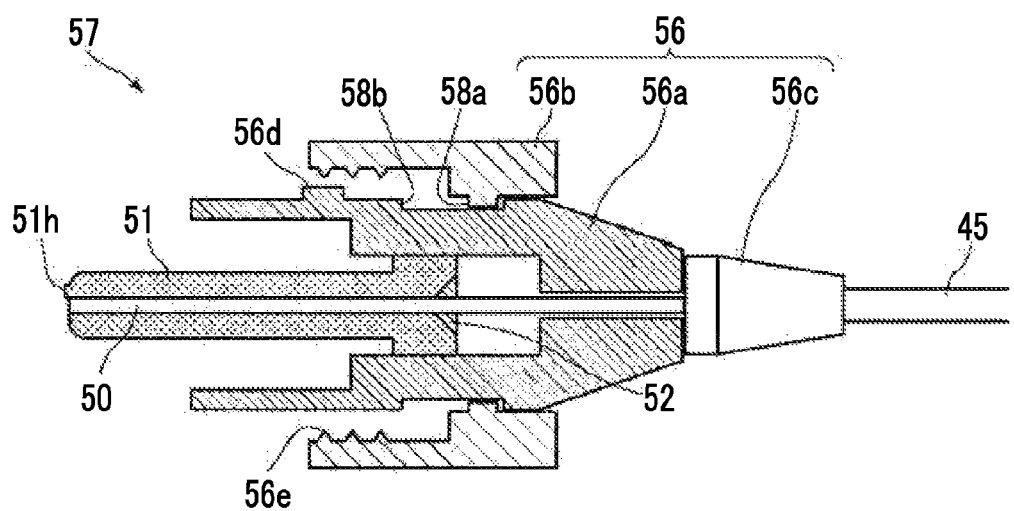
FIG. 11A is a cross-sectional view schematically showing a plug of an optical fiber cable according to a sixth embodiment.
Figure 11B:
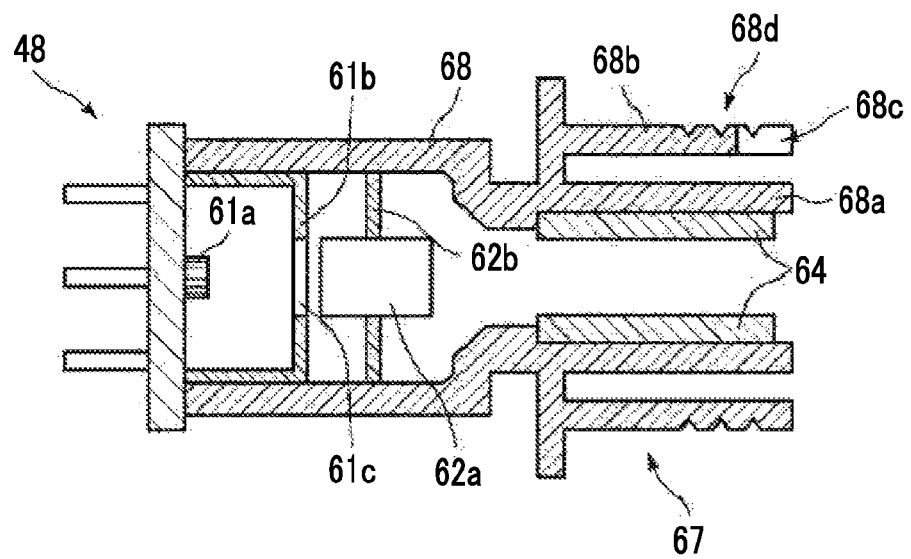
FIG. 11B is a cross-sectional view schematically showing a receptacle of the optical fiber cable according to the sixth embodiment.

Next, a sixth embodiment of the present invention will be described. FIG. 11A is a cross-sectional view schematically showing a plug of an optical fiber cable according to the sixth embodiment, and FIG. 11B is a cross-sectional view schematically showing a receptacle of the optical fiber cable according to the sixth embodiment. In particular, the present embodiment is characterized in that the plug has a ferrule and a housing.

Specifically, a plug 57 on the side of the incidence end portion of the optical fiber cable of the present embodiment has, for example, a screw fastening type FC connector structure conforming to JIS standards, and includes the ferrule 51 and a housing 56. In the ferrule 51, a protruding portion 51h of the positioning structure is formed on the incidence end surface of the ferrule 51, and a burr defect is positioned with the protruding portion 51h as a reference. Other matters regarding the ferrule (for example, materials, a method for fixing to the optical fiber, a specific positioning method of a burr defect, and the like) are the same as those in the first embodiment.

The housing 56 is configured to include a housing body 56a, a fastening screw 56b, and a boot 56c, for example. The housing body 56a holds the ferrule 51. A guide key 56d is formed on the housing body 56a. The guide key 56d corresponds to a guide groove 68c of a receptacle 67 so as to maintain the positional relationship between the short axis direction of the laser light L and the burr defect, and the guide key 56d is fitted into the guide groove 68c when the plug 57 is connected to the receptacle 67. In other words, in consideration of the alignment structure configured to include the guide key 56d and the guide groove 68c, positioning of the burr defect with respect to the protruding portion 51h is performed. As a result, the arrangement of the burr defect with respect to the beam cross section on the incidence end surface of the ferrule 51 is maintained. A protruding portion 58a that protrudes toward the housing body is formed on the fastening screw 56b, and the protruding portion 58a is disposed in a sliding groove 58b formed in the housing body 56a. Therefore, the fastening screw 56b can slide back and forth along the central axis with respect to the housing body 56a within a range in which the protruding portion 58a can move in the sliding groove 58b. In addition, a male screw 56e is formed on the inner peripheral side of the fastening screw 56b, and the male screw 56e is screwed to a female screw 68d of the receptacle 67.

The receptacle 67 is configured to include a shell 68 and a sleeve 64, and the shell 68 has a small-diameter fitting portion 68a for holding the sleeve 64 and a large-diameter fitting portion 68b fitted into the fastening screw 56b. The guide groove 68c and the female screw 68d are formed in the large-diameter fitting portion 68b. In addition, the same LD as in the first embodiment is provided in the opening of the shell 68 on a side opposite to the side where the plug 57 is inserted.

Figure 12:
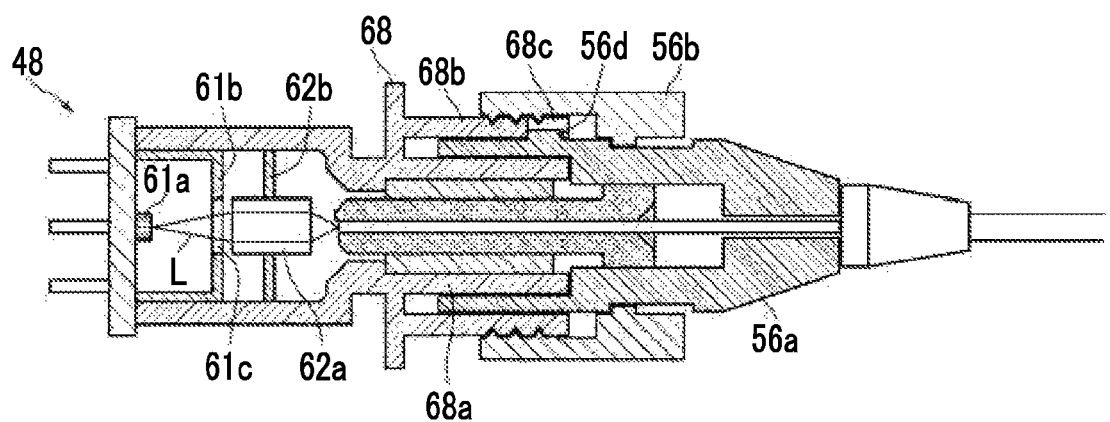
FIG. 12 is a cross-sectional view schematically showing a state in which the plug shown in FIG. 11A is connected to the receptacle shown in FIG. 11B by being inserted thereinto.

FIG. 12 is a cross-sectional view schematically showing a state in which the plug shown in FIG. 11A is connected to the receptacle shown in FIG. 11B by being inserted thereinto. As shown in FIG. 12, the plug 57 is connected to the receptacle 67 so that the guide key 56d is fitted into the guide groove 68c. When the flat-shaped laser light L is emitted from the semiconductor light emitting element 61a in a state in which the plug 57 is connected to the receptacle 67, the laser light L is condensed by the lens 62a provided in the cap 61b, and the condensed laser light L is incident from the incidence end surface of the optical fiber 50.

As described above, also in the light source module according to the present embodiment, it is possible to perform the positioning of the burr defect so that the protruding portion 51h as a positioning structure and the burr defect have a predetermined positional relationship therebetween in consideration of the short axis direction of laser light. As a result, since it is possible to avoid a situation in which a region on which the laser light L is incident overlaps a region where the burr defect 53 is present, the same effect as in the first embodiment is obtained.

In the explanation of the present embodiment, the case where the ferrule has the protruding portion 51h as a positioning structure has been described. However, the present invention is not limited thereto. That is, in a case where the plug has a housing, the positioning structure does not necessarily need to be in the ferrule. For example, in the sixth embodiment, the protruding portion 51h may not be provided. In this case, for example, the guide key 56d of the housing 56 can be used as the positioning structure of the present invention. That is, after an optical fiber is inserted into a ferrule having no positioning structure and only the end surface position is adjusted, a burr defect is disposed at a predetermined position considering the relationship with the guide key 56d when fixing the ferrule to the housing. Thus, the positioning structure may be formed in a plug or the like as long as the positioning structure is present at a position that can be viewed at the time of attachment of the plug to the optical fiber.

In the explanation of the present embodiment, the case where the plug has an FC connector structure has been described. However, the present invention is not limited thereto. For example, the plug on the side of the incidence end portion may have any other connector structures, such as an SC type connector structure, an MU type connector structure, a DS type connector structure, and a DL type connector structure conforming to JIS standards and an ST type connector structure, an LC type connector structure, and an MTRJ type connector structure conforming to IEC standards.

Seventh Embodiment

Figure 13A:
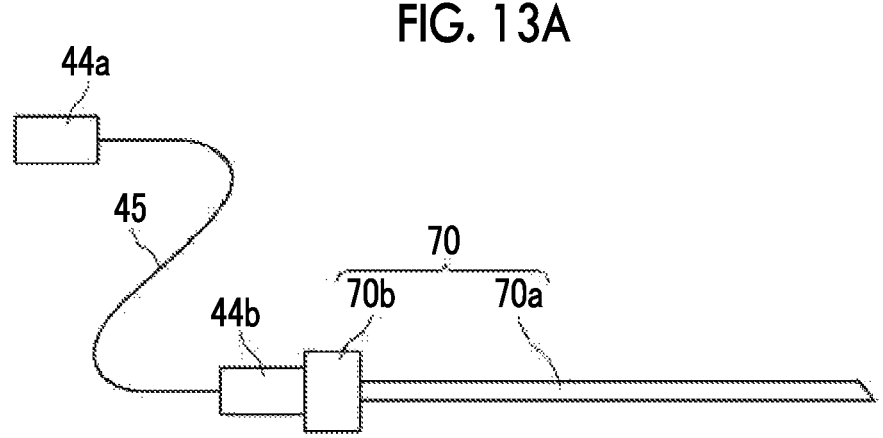
FIG. 13A is a side view schematically showing an optical fiber cable with an insertion needle according to a seventh embodiment.
Figure 13B:
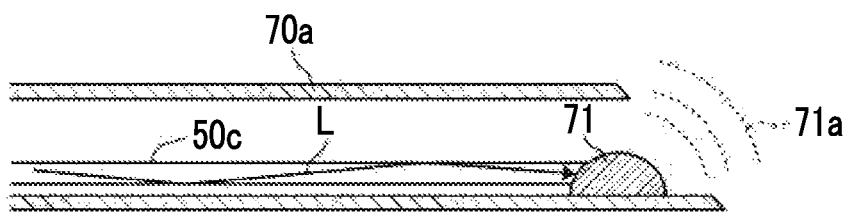
FIG. 13B is a cross-sectional view schematically showing an internal structure of the distal end of the insertion needle shown in FIG. 13A.

Next, a seventh embodiment of the present invention will be described. FIG. 13A is a side view schematically showing an optical fiber cable with an insertion needle according to the seventh embodiment. FIG. 13B is a cross-sectional view schematically showing the internal structure of the distal end of the insertion needle shown in FIG. 13A. In particular, the present embodiment is characterized in that an insertion needle is provided in a region of the optical fiber cable on the emission end portion side of laser light. Other components of the optical fiber cable and a light source unit are the same as those in the first embodiment, for example.

An insertion needle 70 has an insertion needle body 70a and a needle base 70b, for example. The insertion needle body 70a has a tubular structure having an inner cavity thereinside. The distal end portion of the insertion needle body 70a is formed at an acute angle by being cut on a face (cut surface) that is inclined with respect to the central axis of the tubular structure. Accordingly, an opening along the inclined surface is formed in the distal end portion. As a light guide member, for example, an optical fiber 50c having a sufficiently smaller diameter than the diameter of the inner cavity of the insertion needle body 70a is inserted into the inner cavity of the insertion needle 70. The needle base 70b has a connector structure corresponding to the plug 44b, and is configured so as to be detachable and attachable from and to the plug 44b. When the plug 44b is mounted in the needle base 70b, the optical fiber 50 in the plug 44b is optically connected to the optical fiber 50c in the insertion needle 70. Accordingly, the laser light L guided through the optical fiber 50 is incident on the optical fiber 50c, and is then transmitted to the vicinity of the distal end of the insertion needle 70 through the optical fiber 50c. The emission end portion of the optical fiber 50c extends up to the vicinity of the distal end of the insertion needle body 70a. A light absorption member 71 is fixed to the vicinity of the distal end of the insertion needle body 70a, and the emission end portion of the optical fiber 50c is embedded into the light absorption member 71. The position of the emission end portion of the optical fiber 50c may be any position where the laser light L is emitted to the light absorption member 71, and does not necessarily need to be embedded in the light absorption member 71. The light absorption member 71 is formed of, for example, an epoxy resin containing black pigment mixed thereinto, a polyurethane resin, a fluorine resin or silicone rubber, and pewter. Here, the vicinity of the distal end of the insertion needle 70 (or the insertion needle body 70a) means a position where it is possible to generate photoacoustic waves capable of imaging the position of the distal end of the insertion needle with accuracy, which is required for insertion work, in a case where the light emitting portion of the optical fiber 50c and the light absorption member 71 are disposed at the position. For example, the vicinity of the distal end of the insertion needle 70 (or the insertion needle body 70a) indicates a range of 0 mm to 3 mm toward the proximal end side from the distal end of the insertion needle. Also in subsequent embodiments, the meaning of the vicinity of the distal end is the same.

If such an optical fiber cable with an insertion needle is used, it is possible to check the position of the insertion needle in the subject using photoacoustic imaging upon insertion work on the subject. Specifically, this is as follows. First, the operator (for example, a doctor) of the optical fiber cable with an insertion needle connects the optical fiber cable to the light source unit 41, and makes the light source 48 emit the laser light L. The laser light L is guided through the optical fiber 50 and the optical fiber 50c to be absorbed by the light absorption member 71. At this time, a photoacoustic wave 71a due to the light absorption is generated from the light absorption member 71. The operator inserts the insertion needle 70 into the subject, for example, detects the photoacoustic wave propagating through the subject using a probe for ultrasound detection, so that the operator can observe a photoacoustic image based on the detection signal. Therefore, by observing the photoacoustic image, the operator can check where the distal end of the insertion needle 70 is located, that is, how deep the insertion needle has been inserted. Then, the operator removes the plug 44b from the needle base 70b, and collects a sample (for example, blood) from the inside of the subject using the inner cavity of the insertion needle 70.

In the explanation of the present embodiment, the case where the insertion needle body 70a has the light absorption member 71 has been described. However, the present invention is not limited thereto. For example, metal materials, such as stainless steel, aluminum, aluminum alloy, titanium, titanium alloy, and Ni—Ti alloy that are common materials of the insertion needle, and hard resin materials, such as polyimide and polyphenylene sulfide, have a light absorption property. Accordingly, if the insertion needle is formed of a material having a light absorption property, the insertion needle itself can be used as a light absorption member by adjusting the direction of emission of light without providing the light absorption member separately.

Eighth Embodiment

Figure 14A:
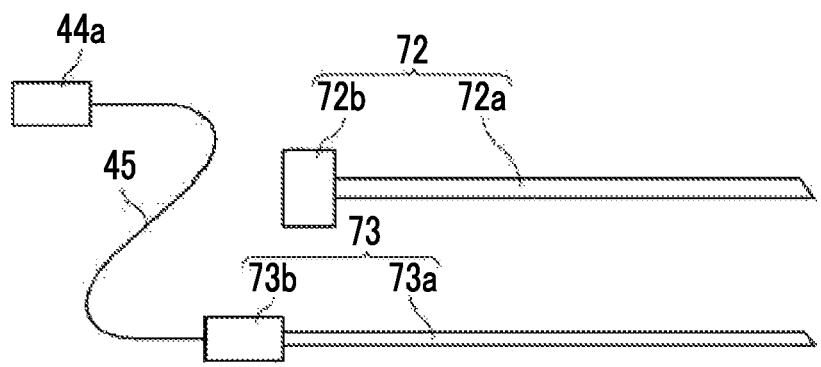
FIG. 14A is a side view schematically showing an optical fiber cable with an insertion needle according to an eighth embodiment.
Figure 14B:
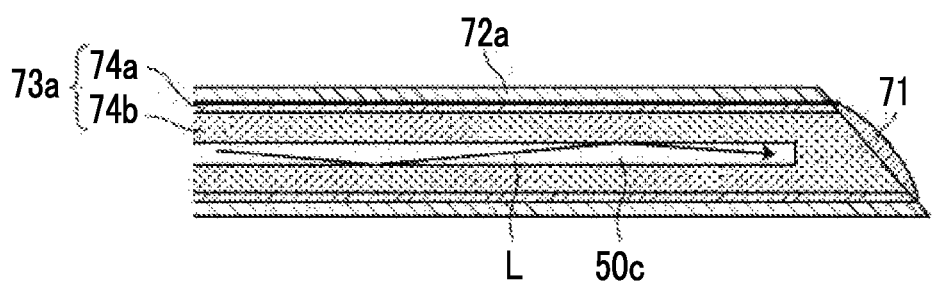
FIG. 14B is a cross-sectional view schematically showing an internal structure (state in which the inner needle is inserted into the outer needle) of the distal end of the insertion needle shown in FIG. 14A.

Next, an eighth embodiment of the present invention will be described. FIG. 14A is a side view schematically showing an optical fiber cable with an insertion needle according to the eighth embodiment. FIG. 14B is a cross-sectional view schematically showing the internal structure (state in which the inner needle is inserted into the outer needle) of the distal end of the insertion needle shown in FIG. 14A. The present embodiment is different from the seventh embodiment in that the insertion needle has an inner needle that seals at least a part of the outer needle. Other components are the same as those in the seventh embodiment, for example.

The insertion needle according to the present embodiment has an outer needle 72 configured to include an outer needle body 72a and an outer needle base 72b and an inner needle 73 configured to include an inner needle body 73a and an inner needle base 73b. The inner needle body 73a has an outer diameter that is approximately the same as the inner diameter of the outer needle body 72a, for example, and is configured so as to be able to be inserted into or removed from the outer needle base 72b side with respect to the hollow outer needle body 72a. The inner needle body 73a is configured to include a tube 74a having a tubular structure and a transparent resin 74b that fills the internal space of the tube 74a. The tube 74a is, for example, a stainless steel tube, a polyimide tube, or a tube formed of fluorine resin, such as polytetrafluoroethylene (PTFE). For example, an adhesive, such as an epoxy resin, is used as the transparent resin 74b. For example, the optical fiber 50c as a light guide member is inserted into the tube 74a. Then, the optical fiber 50c is fixed to the tube 74a by being bonded thereto by filling the space between the optical fiber 50c and the tube 74a with the transparent resin 74b. The optical fiber 50c is optically connected to the optical fiber on the cable side within the inner needle base 73b. Alternatively, the optical fiber 50c is a single optical fiber that is directly connected to the optical fiber on the cable side. A distal end portion of the inner needle body 73a is formed at an acute angle similar to the distal end of the outer needle body 72a. The same light absorption member 71 as in the seventh embodiment is attached onto the cut surface of the inner needle body 73a, and the laser light L emitted from the emission end portion of the optical fiber 50c is emitted to the light absorption member 71. As a result, a photoacoustic wave is generated in the distal end portion of the inner needle 73.

Also by the optical fiber cable according to the present embodiment, it is possible to guide the laser light to the distal end of the insertion needle. Therefore, it is possible to check the position of the insertion needle in the subject using photoacoustic imaging. In the present embodiment, the insertion needle has the inner needle 73 that seals the outer needle 72. In this manner, by clogging the inner cavity of the outer needle 72 with the inner needle 73, the operator can insert the insertion needle into the subject without the insertion feeling being adversely affected.

In the explanation of the present embodiment, the case where the light absorption member 71 is applied onto the cut surface of the distal end of the inner needle 73 has been described. However, the present invention is not limited thereto. For example, in a case where the inner needle body is formed of a material, such as an epoxy resin containing black pigment mixed thereinto, a polyurethane resin, a fluorine resin, or silicone rubber, the inner needle body itself functions as a light absorption member. Therefore, it is not necessary to provide a light absorption member separately.

Although the case where the insert is an insertion needle has been described in the seventh and eighth embodiments, the present invention is not limited to thereto. The insert may be a needle for radiofrequency ablation in which an electrode used in radiofrequency ablation is housed, or may be a catheter inserted into the blood vessel, or may be a guide wire of the catheter inserted into the blood vessel. Alternatively, the insert may be an optical fiber for laser treatment.

[Embodiment of a Photoacoustic Measurement Apparatus]

Figure 15:
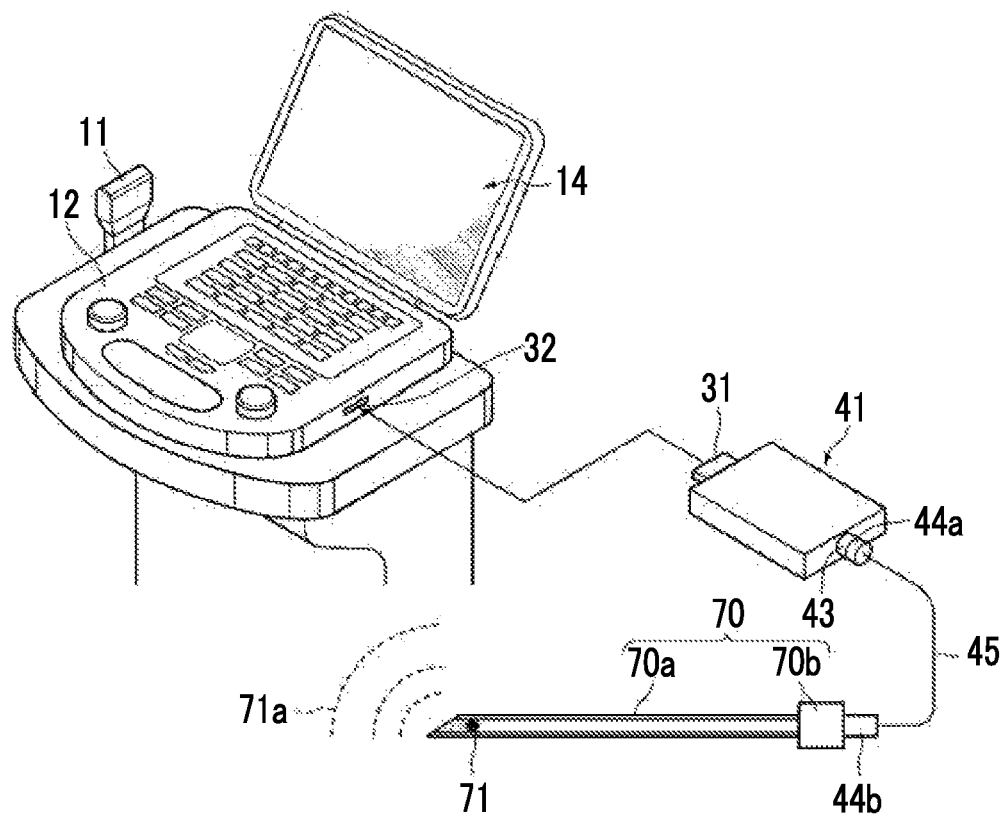
FIG. 15 is a perspective view schematically showing a photoacoustic image generation apparatus (photoacoustic measurement apparatus) including the light source module of the present invention.
Figure 16:
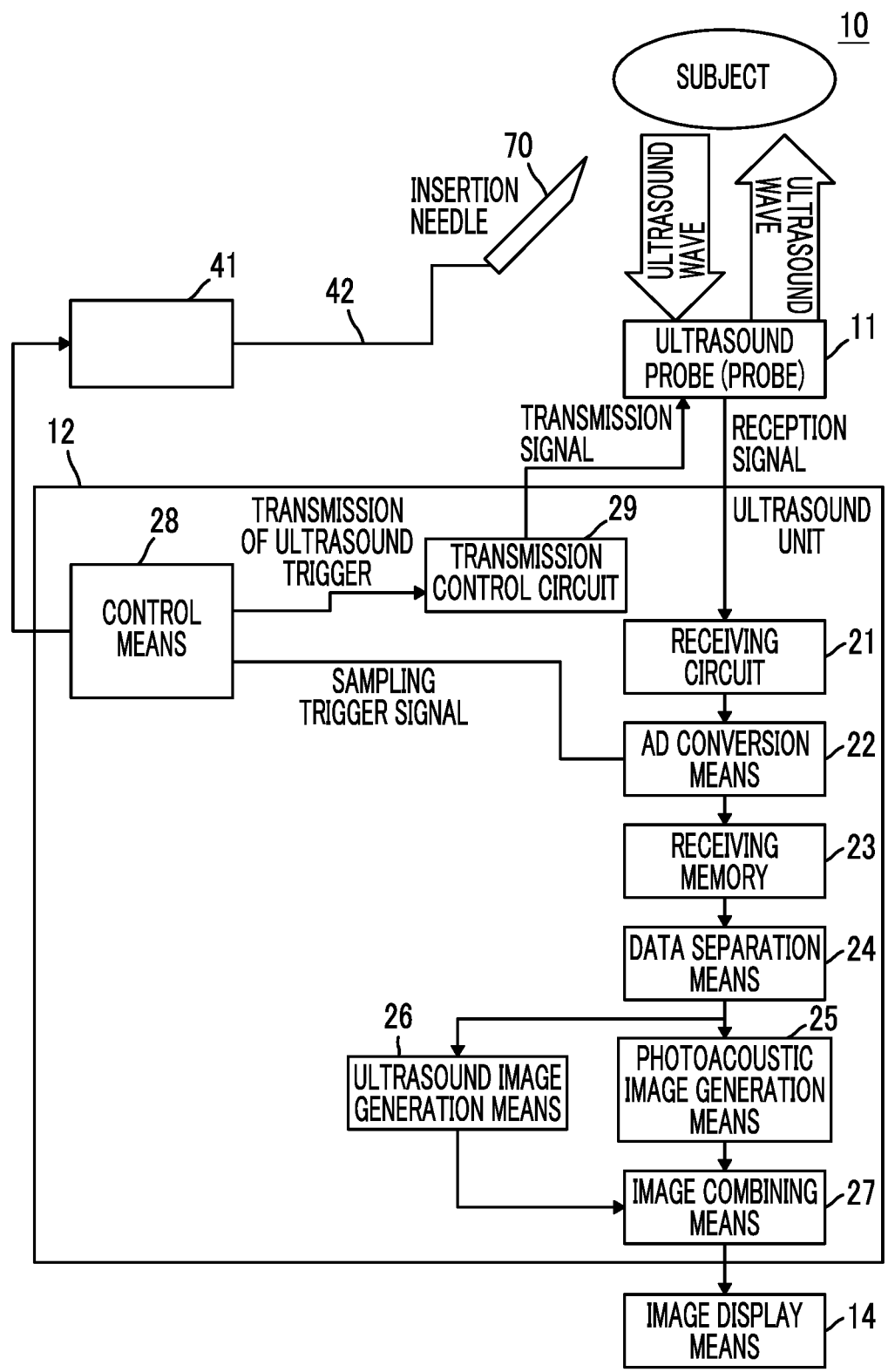
FIG. 16 is a block diagram schematically showing the configuration of the photoacoustic image generation apparatus shown in FIG. 15.
Figure 17:
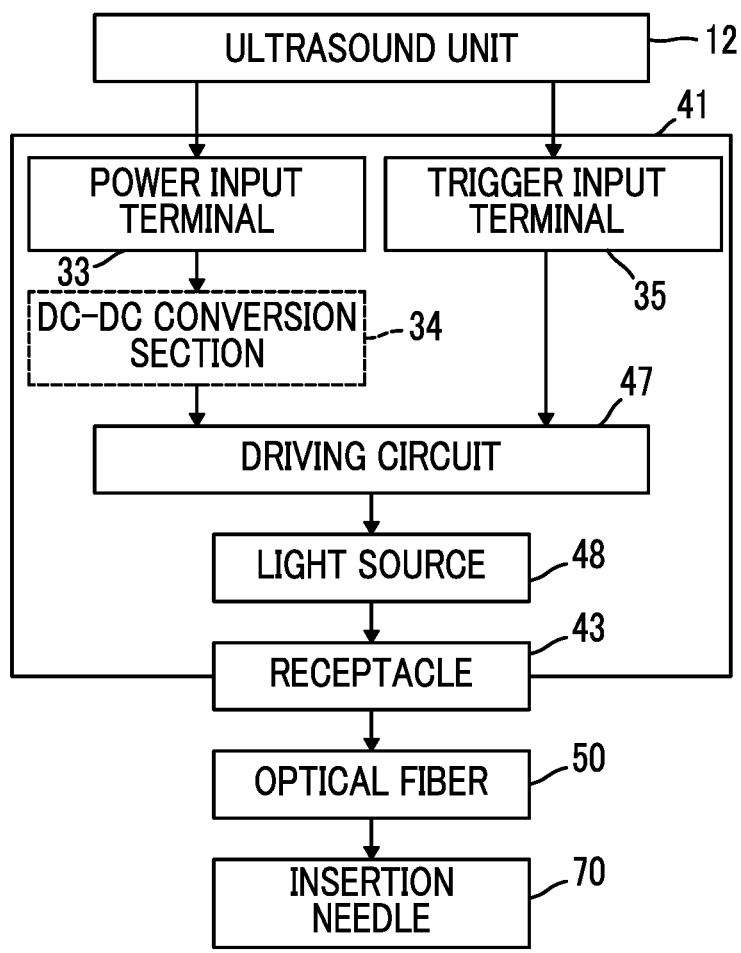
FIG. 17 is a block diagram schematically showing the configuration of the light source unit shown in FIG. 16.

Next, an embodiment of a photoacoustic image generation apparatus as a photoacoustic measurement apparatus of the present invention will be described. The photoacoustic image generation apparatus is an apparatus that generates a photoacoustic image based on the photoacoustic signal detected by the probe (ultrasound probe). FIG. 15 is a perspective view schematically showing a photoacoustic image generation apparatus including the light source module of the present invention. FIG. 16 is a block diagram schematically showing the configuration of the photoacoustic image generation apparatus shown in FIG. 15. FIG. 17 is a block diagram schematically showing the configuration of the light source unit shown in FIG. 16.

A photoacoustic image generation apparatus 10 includes a probe 11, an ultrasound unit 12, and a light source module with an insertion needle. In the embodiment of the present invention, an ultrasound wave is used as an acoustic wave. However, the present invention is not limited to the ultrasound wave, and an acoustic wave having an audible frequency may be used if an appropriate frequency can be selected according to an examination target, measurement conditions, or the like.

As a light source module with an insertion needle, for example, it is possible to use that according to the seventh embodiment. Specifically, the light source module according to the present embodiment is configured to include a light source unit 41, which includes a power input terminal 33, a DC-DC conversion section 34, a trigger input terminal 35, an LD driving circuit 47, a light source 48, and a receptacle 43, and an optical fiber cable with the insertion needle 70.

The power input terminal 33 is connected to the power supply line of the ultrasound unit 12. Direct current (DC) power of, for example, 5 V is supplied to the power input terminal 33. The trigger input terminal 35 is connected to the signal output line of the ultrasound unit 12. The power input terminal 33 and the trigger input terminal 35 are configured as a USB connector, for example. The ultrasound unit 12 has a USB port, for example. By inserting the USB connector including the power input terminal 33 and the trigger input terminal 35 into the USB port, electric power is supplied to the light source unit 41, and a signal output from the ultrasound unit 12 is supplied.

The DC-DC conversion section 34 converts the voltage of DC power supplied from the power input terminal 33. The DC-DC conversion section 34 converts DC 5 V into DC 12 V, for example. The driving circuit 47 drives a semiconductor laser diode as the light source 48. The light source 48 is driven by the DC power supplied from the DC-DC conversion section 34. The driving circuit 47 controls the DC power supplied to the light source 48 based on the trigger signal input from the trigger input terminal 35, so that pulsed laser light is emitted from the light source 48 at a desired timing. The emitted laser light is guided to the insertion needle 70 through the receptacle 43 and the optical fiber 50 in the optical fiber cable.

The pulse energy of the pulsed laser light emitted from the light source unit 41 can be set to 6.4 µJ if the core diameter of the optical fiber is 200 µm. The pulse energy of the pulsed laser light can be set to 2.0 µJ if the core diameter of the optical fiber is 100 µm. The pulse time width can be set to 80 ns. The repetition frequency of a pulse may be set to 60 Hz in the case of performing image display at 30 fps, for example. The repetition frequency can be realized up to 3300 Hz at the highest.

The probe 11 is connected to the ultrasound unit 12. The ultrasound unit 12 is configured as an integrated device including the image display means 14. A program regarding photoacoustic image generation is installed in the ultrasound unit 12. The ultrasound unit 12 has a USB port 32. A USB connector including the power input terminal 33 and the trigger input terminal 35 of the light source unit 41 is inserted into the USB port 32. In a case where the light source unit 41 is a card-sized small and lightweight device, it is possible to hold the USB connector by inserting the USB connector into the USB port of the ultrasound unit 12.

The probe 11 is acoustic wave detection means, and has a plurality of ultrasound transducers arranged in a one-dimensional manner, for example. The probe 11 detects photoacoustic waves generated due to the light emitted from the light source 48 after the insertion needle 70 is inserted into the subject. In addition to the detection of photoacoustic waves, the probe 11 performs transmission of acoustic waves (ultrasound waves) to the subject and reception of reflected acoustic waves (reflected ultrasound waves) of the transmitted ultrasound waves.

The ultrasound unit 12 has a receiving circuit 21, AD conversion means 22, a receiving memory 23, data separation means 24, photoacoustic image generation means 25, ultrasound image generation means 26, image combining means 27, control means 28, and a transmission control circuit 29. The receiving circuit 21 receives a detection signal of the photoacoustic wave detected by the probe 11. In addition, the detection signal of the reflected ultrasound wave detected by the probe 11 is received. The AD conversion means 22 converts the detection signals of the photoacoustic wave and the reflected ultrasound wave, which have been received by the receiving circuit 21, into digital signals. The AD conversion means 22 samples the detection signals of the photoacoustic wave and the reflected ultrasound wave at predetermined sampling periods based on a sampling clock signal having a predetermined period, for example. The AD conversion means 22 stores the sampled detection signals (sampling data) of the photoacoustic wave and the reflected ultrasound wave in the receiving memory 23.

The data separation means 24 separates the sampling data of the detection signal of the photoacoustic wave and the sampling data of the detection signal of the reflected ultrasound wave, which are stored in the receiving memory 23, from each other. The data separation means 24 inputs the sampling data of the detection signal of the photoacoustic wave to the photoacoustic image generation means 25. In addition, the separated sampling data of the reflected ultrasound wave is input to the ultrasound image generation means (reflected acoustic wave image generation means) 26.

The photoacoustic image generation means 25 generates a photoacoustic image based on the detection signal of the photoacoustic wave detected by the probe 11. The generation of a photoacoustic image includes, for example, image reconstruction such as phase matching addition, detection, and logarithmic conversion. The ultrasound image generation means 26 generates an ultrasound image (reflected acoustic wave image) based on the detection signal of the reflected ultrasound wave detected by the probe 11. The generation of an ultrasound image also includes image reconstruction such as phase matching addition, detection, and logarithmic conversion.

The image combining means 27 combines the photoacoustic image and the ultrasound image. The image combining means 27 performs image combination by superimposing the photoacoustic image and the ultrasound image on each other, for example. The composite image is displayed on the image display means 14, such as a display. Without performing image combination, it is also possible to display the photoacoustic image and the ultrasound image on the image display means 14 side by side or to display the photoacoustic image and the ultrasound image by performing switching therebetween.

The control means 28 controls each unit in the ultrasound unit 12. For example, the control means 28 transmits a trigger signal to the light source unit 41 so that the light source unit 41 emits laser light. In addition, the control means 28 controls the sampling start timing of the photoacoustic wave by transmitting a sampling trigger signal to the AD conversion means 22 in response to the emission of the laser light.

In the case of acquiring an ultrasound image, the control means 28 transmits an ultrasound wave transmission trigger signal for giving an instruction of ultrasound wave transmission to the transmission control circuit 29. When the ultrasound wave transmission trigger signal is received, the transmission control circuit 29 makes the probe 11 transmit ultrasound waves. The control means 28 transmits a sampling trigger signal to the AD conversion means 22 according to the timing of ultrasound wave transmission, thereby starting the sampling of reflected ultrasound waves.

FIG. 18 is a flowchart showing the procedure of generating a photoacoustic image using the photoacoustic image generation apparatus 10. Hereinafter, the procedure of generating a photoacoustic image using the photoacoustic image generation apparatus 10 will be described. An operator or the like inserts the insertion needle 70 into the subject (step A1). After inserting the insertion needle 70, the control means 28 of the ultrasound unit 12 transmits a trigger signal to the light source unit 41. When the trigger signal is received, the light source unit 41 starts laser oscillation to emit pulsed laser light. The pulsed laser light emitted from the light source unit 41 is guided to the vicinity of the distal end of the insertion needle 70 by the optical fiber 50, and is absorbed by the light absorption member 71 (step A2).

The probe 11 detects photoacoustic waves generated in the subject due to the emission of the laser light (step A3). The AD conversion means 22 receives detection signals of the photoacoustic waves through the receiving circuit 21, samples the detection signals of the photoacoustic waves, and stores the sampled detection signals in the receiving memory 23. The data separation means 24 transmits the detection signals of the photoacoustic waves stored in the receiving memory 23 to the photoacoustic image generation means 25. The photoacoustic image generation means 25 generates a photoacoustic image based on the detection signals of the photoacoustic waves (step A4).

The control means 28 transmits an ultrasound trigger signal to the transmission control circuit 29. The transmission control circuit 29 makes the probe 11 transmit an ultrasound wave in response to the ultrasound trigger signal (step A5). The probe 11 detects a reflected ultrasound wave after the transmission of an ultrasound wave (step A6). In addition, transmission and reception of ultrasound waves may be performed at separate positions. For example, ultrasound waves may be transmitted from a position different from the probe 11, and reflected ultrasound waves of the transmitted ultrasound waves may be received by the probe 11.

The reflected ultrasound waves detected by the probe 11 are input to the AD conversion means 22 through the receiving circuit 21. Here, the reflected ultrasound wave transmitted from the probe 11 propagates back and forth between the probe 11 and the ultrasound wave reflection position, while the photoacoustic wave propagates through one way from the vicinity of the distal end of the insertion needle 70, which is the generation position, to the probe 11. Accordingly, since the detection of the reflected ultrasound wave requires twice the time for the detection of the photoacoustic wave generated at the same depth position, the sampling clock of the AD conversion means 22 at the time of reflected ultrasound wave sampling may be a half at the time of photoacoustic wave sampling. The AD conversion means 22 stores the sampling data of the reflected ultrasound wave in the receiving memory 23.

The data separation means 24 transmits the detection signal of the reflected ultrasound wave stored in the receiving memory 23 to the ultrasound image generation means 26. The ultrasound image generation means 26 generates an ultrasound image based on the detection signal of the reflected ultrasound wave (step A7). The image combining means 27 combines the photoacoustic image generated in step A4 with the ultrasound image generated in step A7 (step A8). An image obtained by the combination in step A8 is displayed on the image display means 14 (step A9).

In FIG. 15, the receptacle 43 is provided on a surface opposite to a surface on which the USB connector including the power input terminal 33 and the trigger input terminal 35 is present. However, it is preferable that the receptacle 43 is provided on a surface perpendicular to the surface on which the USB connector is present. In a case where the USB connector and the receptacle 43 are provided on the opposite surfaces, if the light source unit 41 is pulled when the operator moves the insertion needle 70, the USB connector may exit from the USB port 32. In contrast, in a case where the USB connector and the receptacle 43 are provided on the surfaces perpendicular to each other, the USB connector is difficult to exit from the USB port 32 even if the light source unit 41 is pulled.

While the present invention has been described based on the preferred embodiment, the optical fiber cable, the method of manufacturing the same, and the light source module including the same of the present invention are not limited to the above embodiment, and various modifications and changes in the configuration of the above embodiment are also included in the range of the present invention.

What is claimed is:

1. An optical fiber cable, comprising:
a plug that is engaged with a receptacle for light emission of a light source unit that emits a light beam having a flat-shaped cross section; and
an optical fiber having a burr defect in a part of an outer peripheral portion of an incidence end surface on which the light beam is incident,
wherein the plug is attached to an incidence end portion of the optical fiber in an arrangement in which the burr defect is located in a short axis direction of a cross section on the incidence end surface of the light beam incident on the incidence end surface in a state in which the plug is engaged with the receptacle.

2. The optical fiber cable according to claim 1,
wherein the plug has a positioning structure for positioning of the burr defect, and
the burr defect is disposed at a position determined in advance in a relationship with the positioning structure.

3. The optical fiber cable according to claim 2,
wherein the plug includes a holding member that has a cylindrical shape having a through hole and that holds the incidence end portion in the through hole, and
the positioning structure is configured to include at least one of a protruding portion, a groove portion, or a flat portion having a surface parallel to a central axis of the optical fiber, all of the protruding portion, the groove portion, and the flat portion being formed on a surface of the holding member.

4. The optical fiber cable according to claim 3,
wherein the positioning structure includes the protruding portion or the groove portion, and
the position determined in advance is a position on a first straight line, which passes through the protruding portion or the groove portion and the central axis, or a position on a straight line, which is perpendicular to the first straight line, in a front view of the holding member.

5. The optical fiber cable according to claim 3,
wherein the positioning structure includes the flat portion, and
the position determined in advance is a position on a second straight line, which passes through the central axis and is perpendicular to a line formed by the flat portion, or a position on a straight line, which is perpendicular to the second straight line, in a front view of the holding member.

6. The optical fiber cable according to claim 3,
wherein the positioning structure is formed in vicinity of an opening of the through hole.

7. The optical fiber cable according to claim 3,
wherein the positioning structure is formed on an outer peripheral surface of the holding member.

8. The optical fiber cable according to claim 3,
wherein the holding member has an air gap structure that forms an air gap extending in at least a long axis direction of the cross section on the incidence end surface from an opening position of the through hole.

9. The optical fiber cable according to claim 8,
wherein the air gap extends up to an outer peripheral surface such that the incidence end portion is viewable in a side view of the holding member.

10. The optical fiber cable according to claim 3,
wherein the plug has a housing member that holds the holding member while maintaining an arrangement of the burr defect with respect to the cross section on the incidence end surface.

11. The optical fiber cable according to claim 1, further comprising:
an insert that is provided on an emission end surface side of the optical fiber and that is inserted into a subject; and
a light absorption member disposed at a position where the light beam emitted from the emission end surface is emitted.

12. The optical fiber cable according to claim 11,
wherein the insert is a needle that is inserted into a subject.

13. A light source module, comprising:
the optical fiber cable according to claim 1;
a light source that emits a light beam having a flat-shaped cross section; and
a receptacle that is engaged with the plug in order to make the light beam, which is emitted from the light source, incident on the incidence end surface.

14. The light source module according to claim 13, further comprising:
an optical system that condenses the light beam emitted from the light source onto the incidence end surface.

15. The light source module according to claim 13,
wherein a long axis diameter of the cross section on the incidence end surface is equal to or greater than ⅓ of a diameter of the incidence end surface.

16. A method of manufacturing an optical fiber cable, comprising:
preparing a plug, which is engaged with a receptacle for light emission of a light source unit that emits a light beam having a flat-shaped cross section, and an optical fiber having a burr defect in a part of an outer peripheral portion of an incidence end surface on which the light beam is incident; and
attaching the plug to an incidence end portion of the optical fiber in an arrangement in which the burr defect is located in a short axis direction of a cross section on the incidence end surface of the light beam incident on the incidence end surface in a state in which the plug is engaged with the receptacle.

17. The method of manufacturing an optical fiber cable according to claim 16,
wherein the plug has a positioning structure for positioning of the burr defect, and
the burr defect is disposed at a position, which is determined in advance in a relationship with the positioning structure, by adjusting an arrangement of the plug and/or the optical fiber before attaching the plug to the optical fiber.

18. The method of manufacturing an optical fiber cable according to claim 17,
wherein the plug includes a holding member that has a cylindrical shape having a through hole and that holds the incidence end portion in the through hole, and
the positioning structure is configured to include at least one of a protruding portion, a groove portion, or a flat portion having a surface parallel to a central axis of the optical fiber, all of the protruding portion, the groove portion, and the flat portion being formed on a surface of the holding member.

* * * * *